United States Patent [19]
Bell et al.

[11] Patent Number: 5,864,056
[45] Date of Patent: Jan. 26, 1999

[54] METHOD AND APPARATUS FOR MONITORING THE COEFFICIENT OF FRICTION BETWEEN A TIRE AND ROLLING SURFACE, PARTICULARLY TO PROVIDE THE VEHICLE OPERATOR WITH COEFFICIENT OF FRICTION, TIRE TREAD WEAR OUT AND SKID WARNING INDICATIONS

[76] Inventors: Larry D. Bell; Christopher D. Bell, both of 4314 Silas Hutchinson Dr., Chantilly, Va. 20151-1328

[21] Appl. No.: 25,096

[22] Filed: Feb. 17, 1998

[51] Int. Cl.$^6$ ................................................ G01M 17/02
[52] U.S. Cl. ............................................................ 73/146
[58] Field of Search ................................................ 73/146

[56] References Cited

U.S. PATENT DOCUMENTS

| | | |
|---|---|---|
| 4,545,240 | 10/1985 | Leiber . |
| 4,779,447 | 10/1988 | Rath . |
| 5,056,354 | 10/1991 | Kuwana . |
| 5,247,831 | 9/1993 | Fioravanti . |
| 5,445,020 | 8/1995 | Rosensweig . |

FOREIGN PATENT DOCUMENTS 0 233 357 A1  8/1987  European Pat. Off. .

OTHER PUBLICATIONS

Tyres, Suspension and Handling by John C. Dixon Cambridge University Press pp. 58–61, 72–75, 85–87, 89–91, 96.

*Primary Examiner*—Joseph L. Felber

[57] ABSTRACT

A method for providing skid warning, a qualitative assessment of the coefficient of friction in the footprint of each tire, and a tire tread wear out indication to a vehicle operator or other automatic systems, is described. The method uses tread force sensors, which can be installed in a tire with minimal changes to tire materials and manufacturing methods, or after tire manufacture. Tread forces within the footprint of a tire are sensed by means of embedded sensors anchored at one end to the tire structure, and at the other end to the tire tread, such that slipping of small discrete tread elements in contact with the roadway can be detected; thereby enabling the determination of the coefficient of friction before the entire footprint slips. Furthermore, coupling of the sensors between the tire structure and the tread within a small area, enables the system to use tire deformation-induced tread gripping forces to determine the coefficient of friction without the presence of maneuvering loads. Tread wear is also determined by monitoring tread slip behavior and tread forces. A suitable system for conveying the tread force information from each tire and converting it into a measure of the coefficient of friction within each footprint, and then generating a skid warning indication, qualitative coefficient of friction and tread wear out displays is provided.

20 Claims, 12 Drawing Sheets

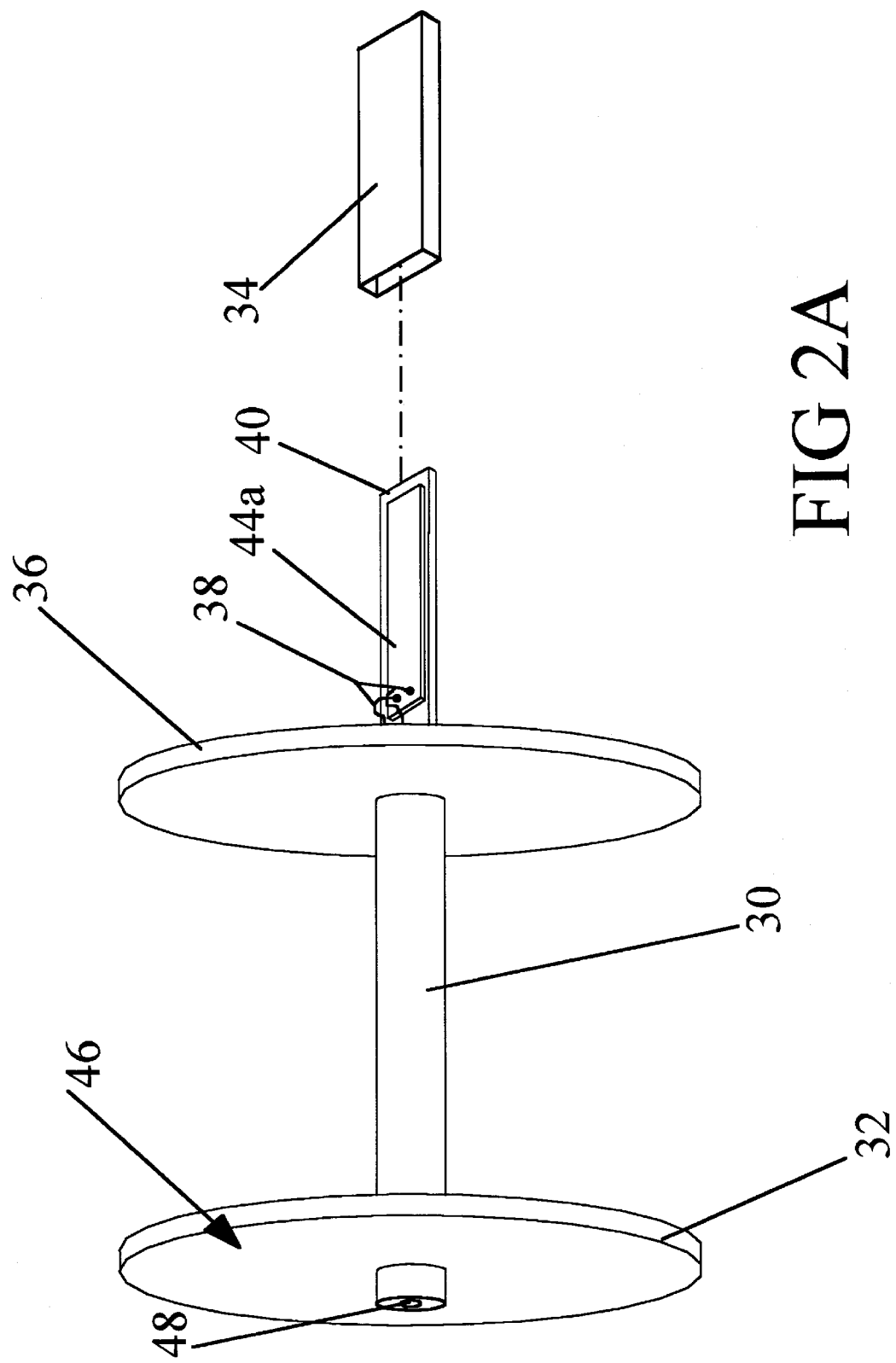

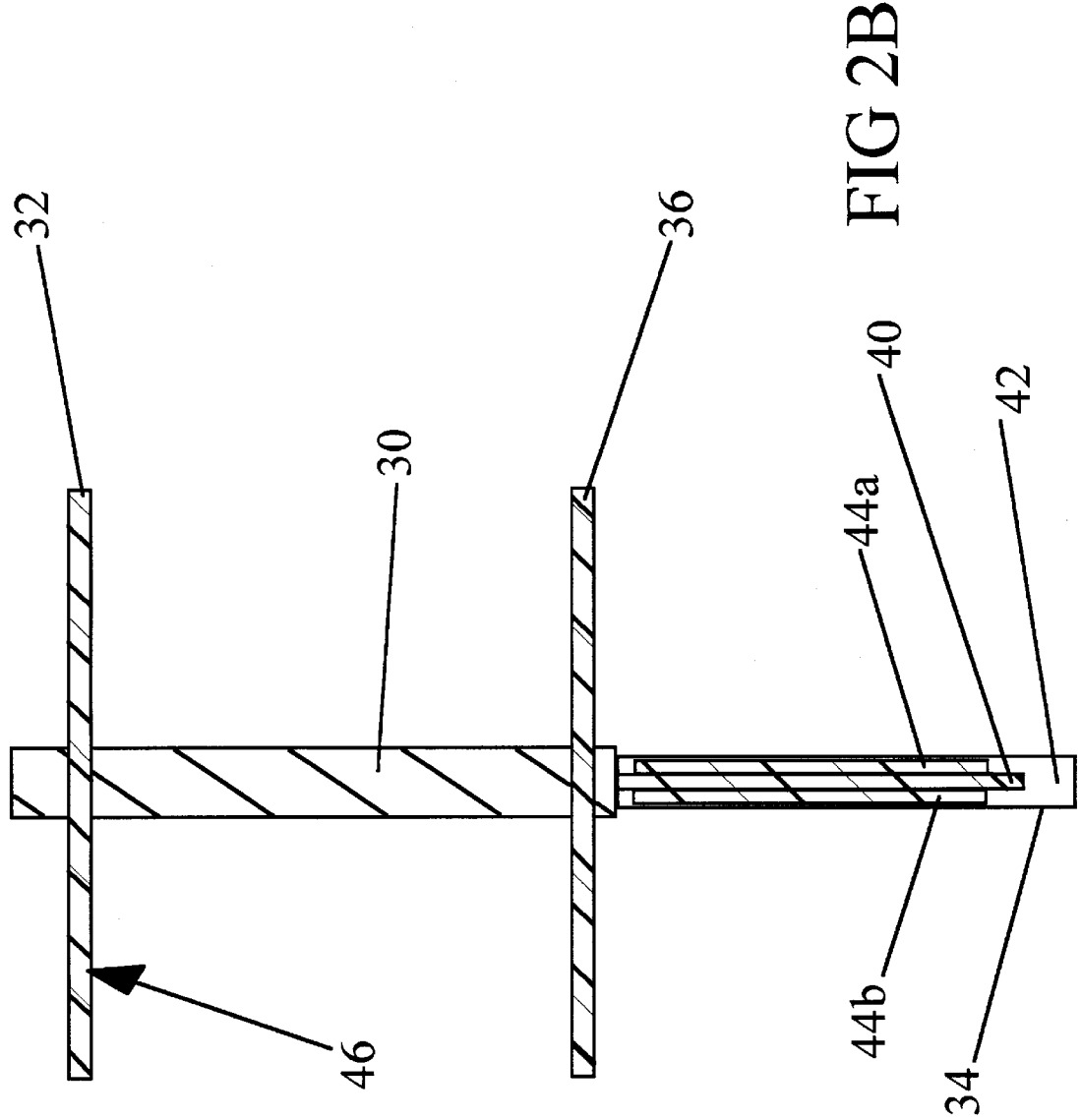

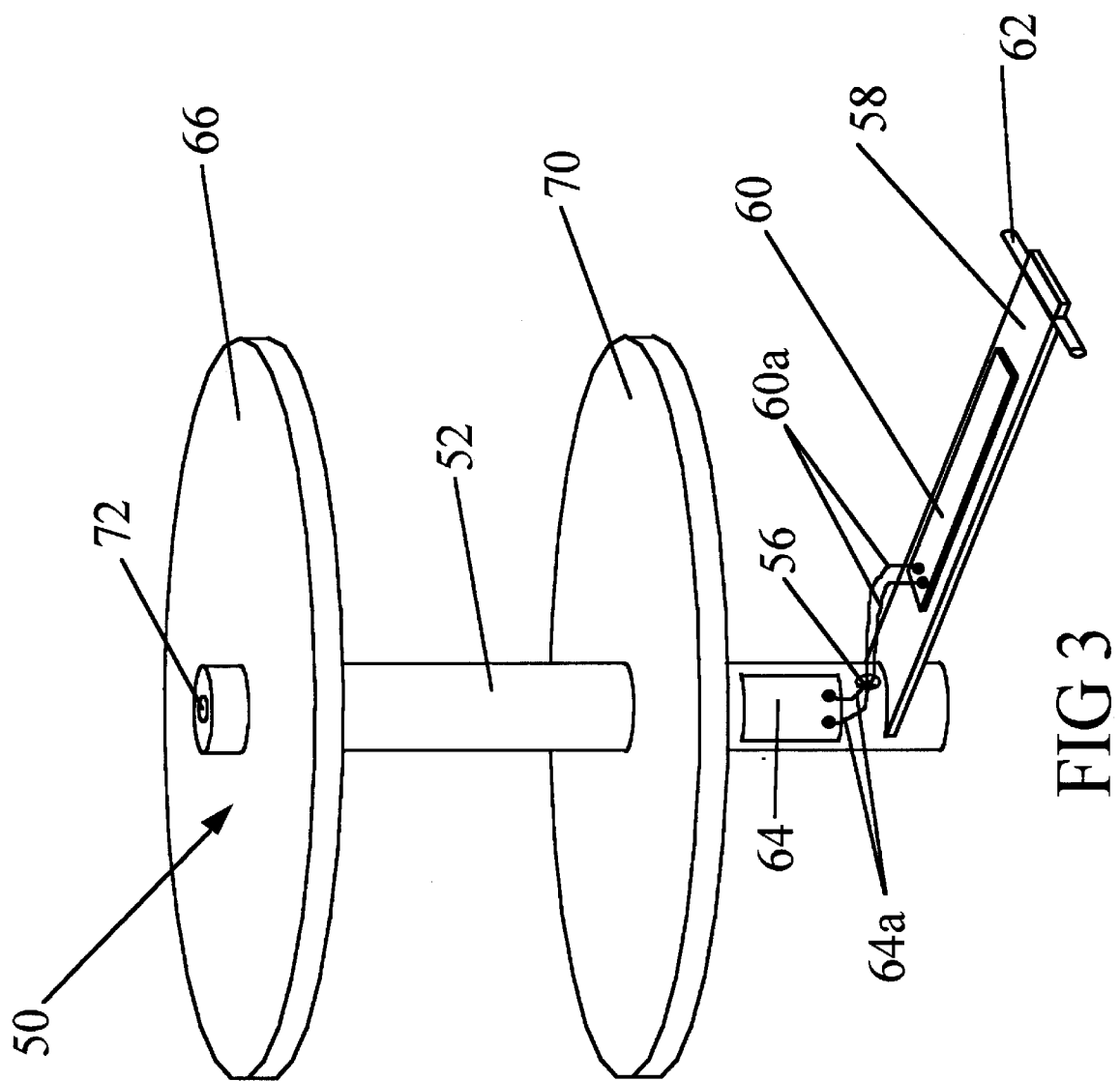

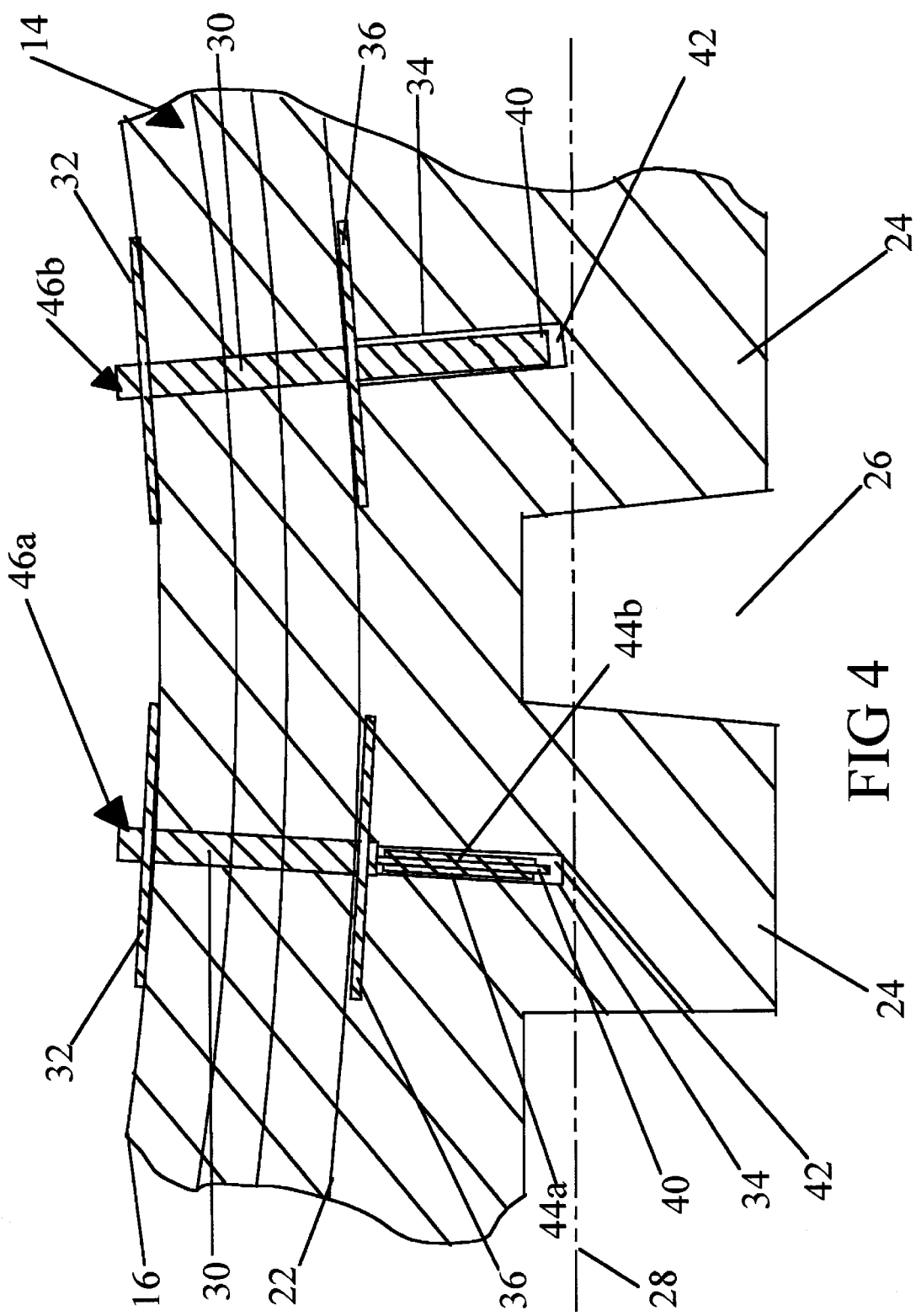

METHOD AND APPARATUS FOR MONITORING THE COEFFICIENT OF FRICTION BETWEEN A TIRE AND ROLLING SURFACE, PARTICULARLY TO PROVIDE THE VEHICLE OPERATOR WITH COEFFICIENT OF FRICTION, TIRE TREAD WEAR OUT AND SKID WARNING INDICATIONS

BACKGROUND

1. Field of Invention

This invention relates to vehicle tires, or other rolling members where it is desirable to monitor the coefficient of friction within the contact area between the rolling member and the rolling surface, and have a skid warning indicator.

2. Description of Prior Art

Since the arrival of automotive anti-skid brake systems and automatic traction control systems, it has become increasingly desirable to monitor the coefficient of friction between a vehicle's tires and the roadway in order to increase vehicle safety and fuel efficiency. The availability of powerful, sturdy computers and processors for automotive applications opens the door for sophisticated automated vehicle performance monitoring and control systems.

Unfortunately, existing methods do not adequately address the problems associated with monitoring the coefficient of friction in the footprint, and do not provide adequate information to the vehicle operator. Specific problems with existing methods include:

(a) measurement of the coefficient of friction requires multiple tires in contact with a roadway; thus continuous knowledge of conditions under individual tires cannot be determined (b) they rely on slip of the entire footprint area (c) the methods are insensitive when the maneuvering forces within the footprint are low (d) they require extensive data processing, and data from multiple types of sensors to remove noise and extract useful coefficient of friction information (e) they require extensive modifications to tire structure and materials to accommodate the tread force sensors (f) they cannot be installed after the tire manufacture is completed (g) they do not provide the vehicle operator with a qualitative indication of the roadway coefficient of friction, nor do they provide a skid warning indication (h) they do not provide an indication of the tread wear and overall tire tread condition, nor do they provide a wearout indication.

Anti-skid braking systems, such as those described by Okazaki in U.S. Pat. No. 5,466,054 (14 Nov. 1995), by Walenty et al in U.S. Pat. No. 4,916,619 (10 Apr. 1990), by Rath in U.S. Pat. No. 4,779,447 (25 Oct. 1988), and by Leiber in U.S. Pat. No. 4,545,240 (8 Oct. 85) determine the coefficient of friction by monitoring the rotation of two or more wheels during braking or acceleration. A difference in wheel rotation is interpreted as slip. The slip information is combined with brake pressures and other parameters to derive an estimate of the coefficient of friction for the slipping wheel. For these systems to provide coefficient of friction information, slippage must occur everywhere within the footprint, and result in a significant change in tire rotational speed. During the slip, the affected wheel is not able to effectively control vehicle motion; therefore vehicle maneuvering forces must be reacted by the other tires. The added load on the remaining tires increases the potential for skid. Furthermore, it is not always obvious which of the two or more tires is slipping since the system is based on a difference in wheel speeds. In addition, these systems do not take the extra step to create and display an indication of coefficient of friction, or skid warning for the vehicle operator.

Other anti-skid systems, such as those described by Kuwana et al in U.S. Pat. No. 5,236,255 (17 Aug. 1993) and by Kuwana et al in U.S. Pat. No. 5,056,354 (15 Oct. 1991) rely upon acceleration sensors to detect wheel slip and have the same disadvantages discussed above.

Methods that measure the forces exerted by the wheel at the tire footprint have been described by Fioravanti in U.S. Pat. No. 5,247,831 (28 Sep. 93) and in European patent EP-A-0 233 357. Fioravanti's method requires extensive modifications to conventional tire structure, materials and construction methods to allow the incorporation of flexible toroidal strain sensors within the tire structure. They cannot be installed in a tire after it has been built since the sensors are an integral part of the tire structure. These modifications will force tire manufacturers to change their processes extensively and will adversely affect tire performance because Fioravanti's method requires the use of extensometric transducers constructed of piezoresistive rubbers within the tread. Such materials do not have suitable wear characteristics for an automotive tire, and the materials are not readily blended or integrated with existing tire tread manufacturing materials and manufacturing techniques. The fact that tires such as those described by Fioravanti do not exist on the commercial market today, is evidence of the manufacturing problems inherent in the design. There are also significant operational problems with Fioravanti's design. The sensors are excessively sensitive to tire tread forces resulting from maneuvering loads, tire pressure changes, centrifugal forces and tire tread deformation within the footprint. The sensitivity results, in part, from the coupling of tire structure forces into the tread sensors. For example, as the tire pressure, or rotational speed changes, the tire structure will expand, forcing the tread to expand as well. This expansion will influence the tread sensor output and will be indistinguishable from tread forces caused by maneuvering loads without additional sensor information and signal processing. This is to be expected since the sensors described by Fioravanti were intended primarily to determine the full range of forces acting on the tire tread within the footprint. Fioravanti's sensors are not optimized for the determination of the coefficient of friction in the footprint. Additional sensors to measure tire pressure, tire temperature and vehicle acceleration will be required to extract useful coefficient of friction information, and due to the number, and magnitude, of forces acting on the tread sensors, it requires significant processing to extract coefficient of friction information and eliminate noise.

European patent EP-A-0 233 357 documents a method wherein sensors are connected between the wheel rim (or tire bead) and the inside of the tire. This methods has drawbacks similar to Fioravanti's; however, it has the added problem of being coupled entirely to the tire structure, (specifically the inside of the pneumatic tire such as indicated by 16 of FIG. 1), rather than the tread itself. This will make it unsuitable for sensing tire tread slip under light maneuvering loads. Like those already discussed, these systems do not take the extra step to create and display an indication of coefficient of friction, or a skid warning for the vehicle operator.

None of the known methods are designed to take advantage of the tire gripping forces that are a natural result of a pneumatic, or otherwise elastic, tire that is deforming under a load as it rolls on the roadway.

Objects and Advantages

Accordingly, several objects and advantages of our invention are:

(a) to provide a method and system to determine the coefficient of friction within the footprint of a single tire in contact with a rolling surface, at least once each revolution, by monitoring only a discrete element of the tread within the footprint such that the forces present on that discrete element of tread are sensed as the discrete element passes through the footprint. Slipping of the tread is determined by a change in the forces on the discrete tread elements that are not associated solely with the discrete element entering or leaving the footprint.

(b) to provide a method to detect the slippage of a discrete element of the tread within the footprint of a rolling tire, that does not require slippage of all tread within the footprint. In other words, slippage of the entire footprint area, and a resultant change in wheel rotational speed is not required to determine the coefficient of friction in the footprint.

(c) to provide a method of monitoring the forces on a discrete element of tread within the footprint of a rolling tire sensitive enough to detect the slippage of that discrete element of tread under very light maneuvering loads, or by sensing the gripping forces of the pneumatic tire under approximately zero maneuvering loads.

(d) to provide a method of detecting the forces on a discrete element of tread within the footprint of a rolling tire while isolating the sensor from stresses and forces in the tire structure; thus minimizing the ability of various noise sources to couple into the sensor, reducing the processing required to extract meaningful coefficient of friction information, and eliminating the need for information from other sensors (such as accelerometers, tire temperature sensors, and tire pressure sensors).

(e) to provide a method of detecting the forces on a discrete element of tread within the footprint of a rolling tire by means of a sensor assembly that can be incorporated into a conventional tire without extensive redesign of the tire structure, or the tread materials.

(f) to provide a method of detecting the forces on a discrete element of tread within the footprint of a rolling tire by use of a sensor assembly that can be installed in a tire after the tire manufacture is completed.

(g) to provide a system whereby the coefficient of friction is determined from the forces sensed in a discrete element of tread within the footprint of a rolling tire, such that the coefficient of friction is presented to the vehicle operator of the vehicle in the form of a qualitative assessment of roadway coefficient of friction as well as a skid warning indication.

(h) to provide a tire wear out indication and overall assessment of tread condition.

Further objects and advantages are: to provide improved roadway coefficient of friction information to existing anti-skid braking systems, automatic traction control systems and other systems designed to improve the handling of a vehicle or which would benefit from roadway coefficient of friction information, and to provide the ability to sense slippage in lightly loaded wheels, tires and rollers such as those used in the paper milling and copier industries to feed and guide paper.

Further objects and advantages of our invention will become apparent from consideration of the drawings and ensuing description.

DESCRIPTION OF DRAWINGS

FIG. 2A shows a perspective view of the preferred embodiment of the tread force sensor.

FIG. 2B shows a cross-section of the preferred embodiment of the tread force sensor.

FIG. 3 shows a perspective view of an alternate embodiment of the tread force sensor.

FIG. 4 shows a cross-section of a typical pneumatic automobile tire with the preferred embodiment of the tread force sensor integrated into the tire structure. The two identical sensors have their reeds oriented about 90 degrees to each other such that one is sensitive to in-track slippage (parallel to the tire plane of rotation), and the other is sensitive to cross-track slippage (perpendicular to the tire plane of rotation).

Figure 1:
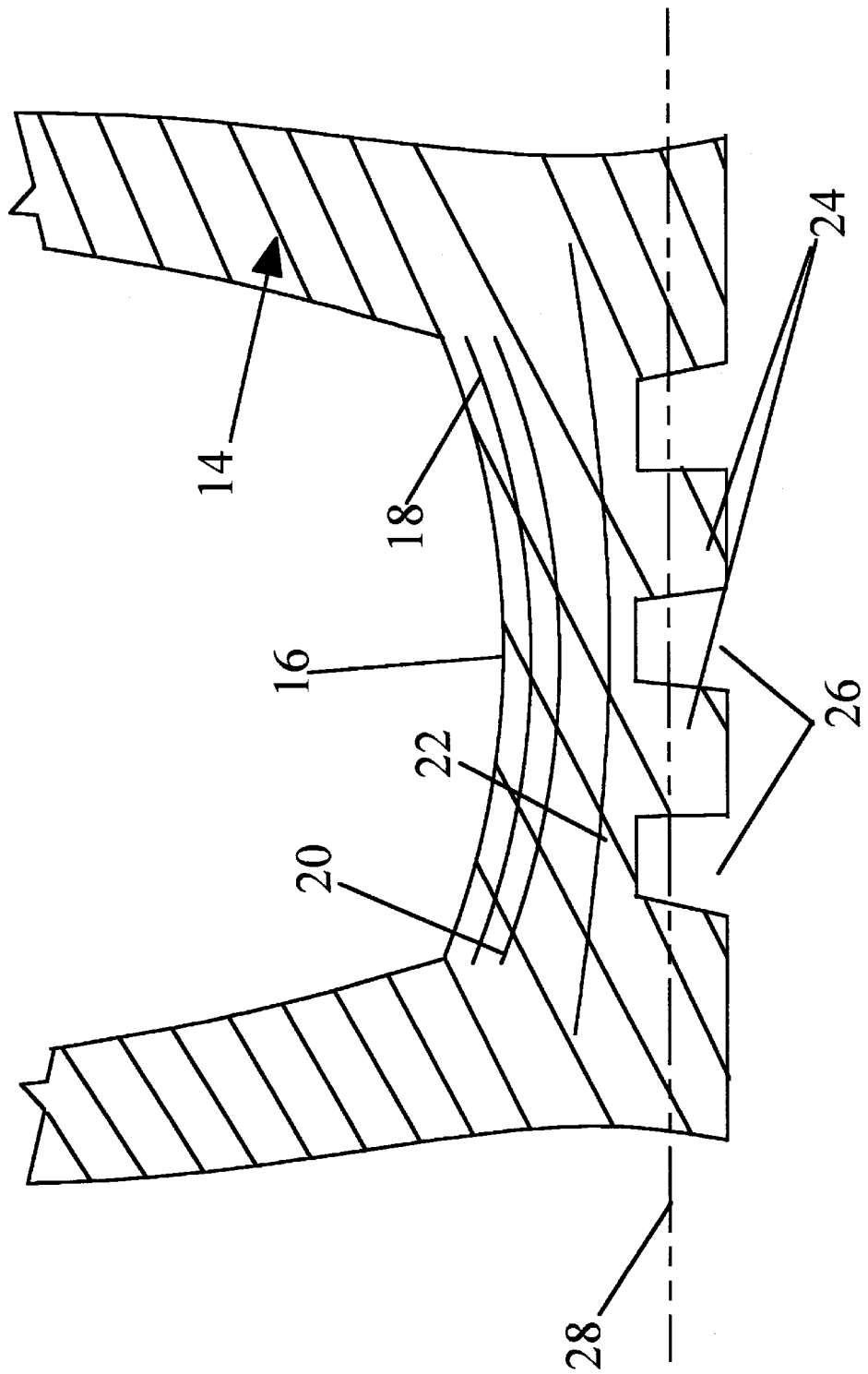
FIG. 1 shows a cross-section of a typical pneumatic automobile tire illustrating the layers and belts that make up the tire structure. Also shown is a representation of a tread pattern.

LIST OF REFERENCE NUMERALS IN DRAWINGS 14 cross-section of typical automobile pneumatic tire
16 inner surface of tire structure
18 representative inner belt in tire structure of typical automobile pneumatic tire cross-section
20 representative mid-layer belt in tire structure of typical automobile pneumatic tire cross-section
22 representative outermost belt tire structure of typical automobile pneumatic tire cross-section
24 cross-section of discrete tread element that contacts roadway 26 tread channel, between discrete tread elements where tread does not touch roadway
28 minimum tread line, indicating the point where tire is at end of useful life
30 structural anchor tube and wire feed-though (preferred embodiment of sensor)
32 inner anchor disk, (rests against inner surface of tire)
34 flexible, low abrasion protective sleeve
36 outer anchor disk, (rests against outer belt of tire structure)
38 Strain gage lead wires for gage 44*a*
40 elongated reed (preferred embodiment of sensor)
42 air gap between end of reed (28) and tread material
44*a* temperature compensated strain gage
44*b* temperature compensated strain gage
46 tread force sensor assembly (preferred embodiment of sensor)
46*a* tread force sensor assembly with reed oriented such that reed face is about parallel to tire plane of rotation
46*b* tread force sensor assembly with reed oriented such that reed face is about perpendicular to tire plane of rotation
48 wire feed-through hole
50 tread force sensor assembly (alternate embodiment of sensor)
52 structural anchor tube and wire feed-through (alternate embodiment of sensor)
56 wire feed-through hole—tube side
58 elongated reed (alternate embodiment of sensor)
60 temperature compensated strain gage
60*a* strain gage lead wires for gage 60
62 reed anchor
64 temperature compensated strain gage
64*a* strain gage lead wires for gage 64
66 inner anchor disk (rests against inner belt of tire structure)
68 contact force sensor assembly
70 outer anchor disk (rests against outer belt of tire structure)
72 wire feed-through hole
74 temperature compensated strain gage
76 strain gage lead wires
78 wire feed-through hole
80 inner anchor disk (rests against inner belt of tire structure)
82 structural anchor tube and wire feed-through, (contact force sensor)
84 outer anchor disk (rests against outer belt of tire structure)
86 force distribution disk
88 wire feed-through hole
90 Tread Force Sensor parallel to tire plane of rotation, and wheatstone bridge circuit
92 Optional tire Temperature Sensor
94 Tread Force Sensor perpendicular to tire plane of rotation, and wheatstone bridge circuit
96 Contact Force Sensor and wheatstone bridge circuit
98 Signal Conditioner and amplifier for sensor perpendicular to tire plane of rotation
100 Signal Conditioner and amplifier for sensor parallel to tire plane of rotation
102 Signal Conditioner and amplifier for Optional Tire Temperature Sensor
104 Signal Conditioner and amplifier for Contact Force Sensor
106 Slip Ring Assembly
108 Data Storage Device
110 Processor
112 Skid Warning Indicator
114 Coefficient of friction Indicator
116 Interface to other vehicle systems that can use coefficient of friction information
118 Tire Tread Force Sensor and wheatstone bridge circuit, alternate embodiment of sensor
120 Contact Force Sensor and wheatstone bridge circuit, alternate embodiment of sensor
122 Interface to other tire slip-rings
124 Tire tread wear out indicator

SUMMARY

A method for providing skid warning, a qualitative assessment of the coefficient of friction in the footprint of each tire, and a tire tread wear out indication to a vehicle operator or other automatic systems, is described. The method uses tread force sensors, which can be installed in a tire with minimal changes to tire materials and manufacturing methods, or after tire manufacture. Tread forces within the footprint of a tire are sensed by means of embedded sensors anchored at one end to the tire structure, and at the other end to the tire tread, such that slipping of small discrete tread elements in contact with the roadway can be detected; thereby enabling the determination of the coefficient of friction before the entire footprint slips. Furthermore, coupling of the sensors between the tire structure and the tread within a small area, enables the system to use tire deformation-induced tread gripping forces to determine the coefficient of friction without the presence of maneuvering loads. Tread wear is also determined by monitoring tread slip behavior and tread forces. A suitable system for conveying the tread force information from each tire and converting it into a measure of the coefficient of friction within each footprint, and then generating a skid warning indication, qualitative coefficient of friction and tread wear out displays is provided.

DESCRIPTION OF PREFERRED EMBODIMENT OF TREAD FORCE SENSOR

A cross-section of a typical pneumatic automobile tire, 14 is shown in FIG. 1 where 16, 18, 20, and 22 illustrate the internal, multi-layer construction commonly used in such tires. The belts used in the structure of a typical tire are represented by 18, 20 and 22, where 22 represents the outermost belt. The inner surface of the tire structure is shown by 16. The pneumatic cavity of the tire is the area between the tire side-walls and adjacent to the inner surface of the tire 16. The discrete elements of the tread that contact the roadway are illustrated by 24, and the tread channels, or grooves are illustrated by 26. The tread channels, or groves 26 physically separate the tread elements 24; thus permitting them to move and slip independently at the road surface. It is the monitoring of these discrete tread elements that is key to the skid warning system discussed herein. The phantom line, 28 shows the minimum remaining tread at the end of the tire's useful service life. Use of the tire in contact with a roadway or other rolling surface results in tread wear due to abrasion with the road surface. When the tread wear reaches, or goes beyond the phantom line 28, the tire is considered worn out, and should be replaced.

FIG. 2A shows the preferred embodiment of a tread force sensor 46. Sensor 46 consists of a rigid, preferably steel, structural anchor tube and wire feed-through 30 with a flexible, preferably steel, elongated reed 40 attached to one end as shown. Reed 40 is rigidly attached to tube 30 by welding or other-suitable means whereby the wire feed-through hole 48 that runs the full length of tube 30 is not blocked. The width of reed 40 is such that a temperature-compensated strain gage element 44*a* and 44*b*, shown in FIG. 2B, will fit entirely on each side of reed 40; yet narrow enough to allow a rigid outer anchor disk 36 to pass over it during installation into the tire as described later. The outside surface of tube 30 is threaded along a quarter of its length on the end where reed 40 is attached. An inner anchor disk 32 is rigidly attached to tube 30 on the end opposite reed 30, and disk 36 is threaded to accept tube 30. Rigid, preferably steel, anchor disks 32 and 36 have center holes sized to accept tube 30 with a tight fit. Strain gage elements 44a and 44b are attached to both sides of reed 40 by means of a suitable adhesive, and strain gage element lead wires 38 are routed through a wire feed-through hole 48 that runs the full length of tube 30. Gages 44a and 44b, and reed 40 materials and thicknesses are selected to ensure the required cycle life and signal output amplitude for the intended tire and tire application. The combined length of tube 30 and reed 40 are such that the outer end of reed 40 extends as far as possible into the discrete tread element 24 but does not extend beyond the minimum tread line 28 shown in FIG. 4. Gages 44a and 44b, and lead wires 38 are coated with a layer of protective material such as is widely used for encapsulating foil strain gages. Such materials and application processes are widely known and not discussed herein. A flexible, low abrasion protective sleeve 34 made of a material such as PTFE, slips over and completely covers reed 40 and gages 44a and 44b and their lead wires 38. The protective sleeve 34 loosely conforms to the surface of the gages 44a and 44b; yet does not touch the narrow side of reed 40.

FIG. 2B shows a cross-section of sensor 46 oriented to show the arrangement of both gages 44a and 44b on reed 40. Protective sleeve 34 covers reed 40 and gages 44a and 44b, protruding beyond the length of reed 40 such that an air gap 42 exists between the end of reed 40 and the end of protective sleeve 34.

FIG. 4 shows the installation of sensor assembly 46 in a typical pneumatic automotive tire 14. Two orientations of identical sensors 46 are shown: 46a and 46b. Sensor 46a is oriented such that forces within the footprint acting perpendicular to the tire's plane of rotation will deflect reed 40. Sensor 46b is oriented such that forces within the footprint acting parallel to the tire's plane of rotation will deflect reed 40. The number of sensors required in the tire depends upon the fidelity of coefficient of friction information desired, as well as the type of tire. At least one force sensor 46 (in FIG. 2A), per tire is required.

In the preferred embodiment, sensor 46 (FIG. 2A) is installed in the tire structure before the tread is applied and before the tire structure is cured. A typical installation would be accomplished as follows. A minimum of one sensor assembly 46 (FIG. 2A) is inserted through the belted layers 18, 20 and 22 of the uncured tire structure. As shown in FIG. 4, sensors 46a and 46b are inserted through the tire structure, from the inside of the tire, such that reed 40 and gages 44a and 44b of the respective sensors 46a and 46b extend beyond the outermost belt 22 and into the region where the tread will be applied. This is done with disk 36 removed from tube 30 and disk 32 rigidly attached to tube 30. Once each sensor 46a and 46b is inserted into the tire structure, disk 36 is threaded on to tube 30 and tightened such that each sensor 46a and 46b is rigidly clamping and sandwiching the tire structure between their disks 32 and 36. The orientation of sensor 46 (FIG. 2A) must be such that both in-track and cross-track forces are sensed. This can be done by orienting sensors 46 in pairs 46a and 46b (as shown in FIG. 4) with their reeds 40 oriented at about 90 degree angles to each other as already described; or by using a single sensor 46 (FIG. 2A) with the reed 40 oriented at about a 45 degree angle to the tire plane of rotation. As shown in FIG. 2B and FIG. 4, once all sensors are secured in place and oriented, protective sleeve 34 is installed over reed 40 and gages 44a and 44b, and secured in place with a suitable flexible adhesive. The tire tread is then applied, and the tire cured using means that are fully known and not discussed herein. After the tread is cured, wire feed-through hole 48 is potted with epoxy or other suitable adhesive to prevent wire chaffing and to seal hole 48.

Sensor 46 (FIG. 2A and 2B) can also be installed into an existing tire by creating a hole in the tire structure from the inside of the tire to allow sensor 46 to be inserted into the tire. Orientation of reeds 40 and gages 44a and 44b are accomplished as discussed above. Sensor 46 is inserted into the preformed hole created as described above; however, disk 36 is necessarily omitted. Sensor 46 is secured to the inner wall 16 of the tire by a suitable adhesive applied between disk 32 and the inner tire surface 16, and in the preformed tire hole to secure tube 30 to the tire 14.

Figure 11:
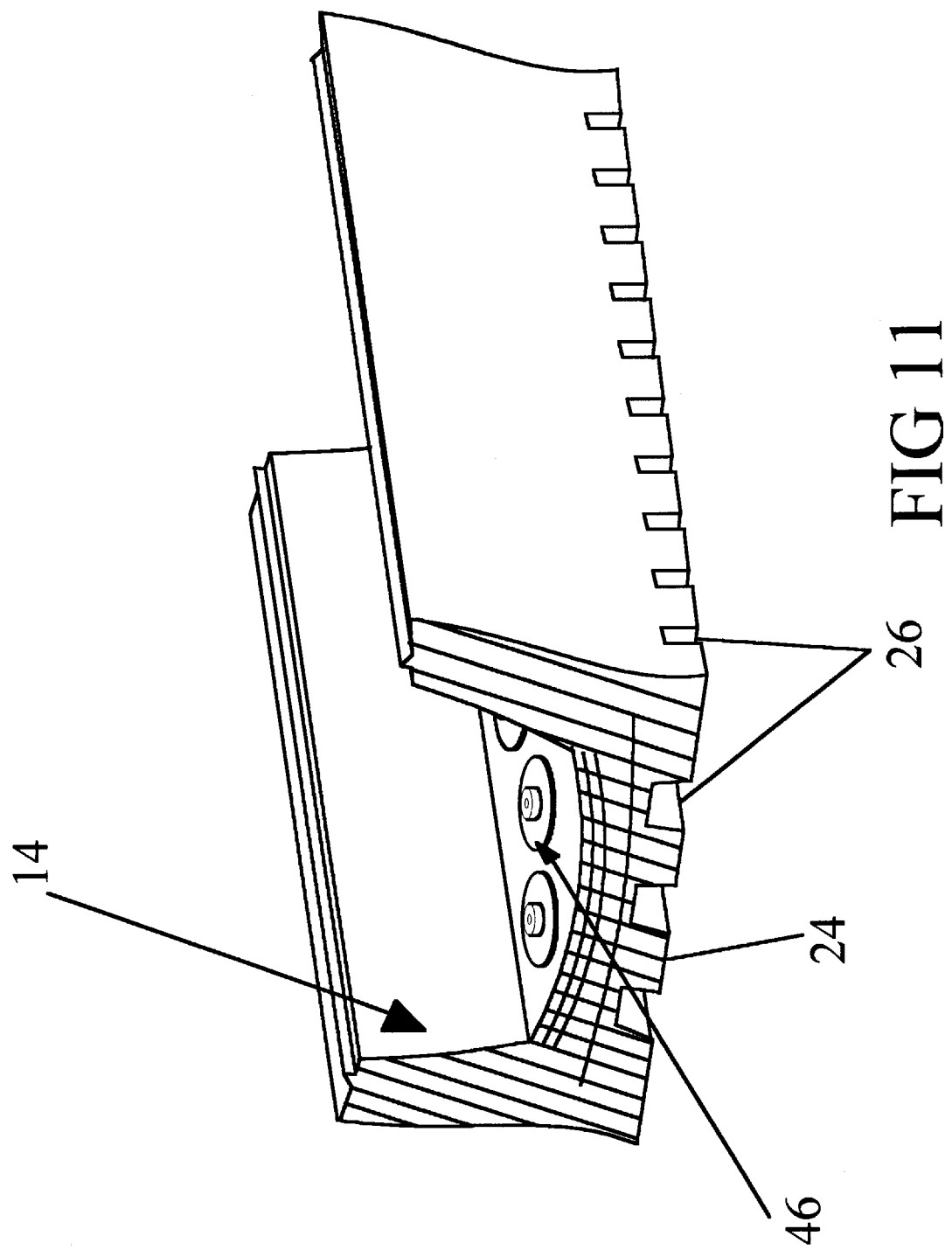
FIG. 11 shows a cross-section of a typical pneumatic automobile tire with the tread force sensors integrated into the tire structure.

FIG. 11 shows a perspective view of a tire section as it will appear after the installation of multiple tread force sensor assemblies 46.

Operation of Preferred Embodiment of Tread Force Sensor

Theory of Operation

Friction is a force which resists motion, or attempted motion, between two bodies pressed together by a force perpendicular to the contact plane. It always acts parallel to the contacting surfaces. It is the friction between a tire and the roadway that permits an automobile to maneuver safely and efficiently. The relation between the perpendicular contact force, N and the friction force in the contact plane, F is:

$$F = C_f * N$$

where $C_f$ is defined as the coefficient of friction. When an automobile rests on a roadway, the contact force N is the portion of the automobile's weight resting on each tire as distributed across the contact area. If $C_f$ and N are known, the magnitude of the force, F that the tire can exert parallel to the footprint without slipping, can be determined from the above equation. The ability to determine the force, F is useful to vehicle operators, and many of the automatic systems in a vehicle. For example, a vehicle operator needs to know whether the vehicle is moving on a dry surface or an icy surface so that the vehicle speed and following distances can be adjusted for safe operation.

The first step toward providing coefficient of friction information to the vehicle operator and other vehicle systems requires a sensor to sample the tire/roadway interface. The tread force sensors described above provide the capability to sense forces on the tread by means of strain gages mounted to a mechanical support system, which is integrated with a tire. The sensor is integrated into the tire, as described above, such that roadway forces acting on the tread and resisted by the tire structure (or vice versa) will result in an electrical signal output from the sensors that is proportional to the force. From this signal, the forces can be derived by well known means that are not discussed herein. The purpose of anchoring the sensors to the tire structure near the discrete tread element to be monitored is to minimize the ability of forces acting within the primary tire structure (i.e. the belted layers) to couple into the sensor. Keeping the sensors in a small region at the interface between the tread layer and the outermost belted layer of the tire structure allows the tire structure to flex, expand and contract under centrifugal and maneuvering forces with minimal influence on the tread force sensors. The sensors achieve their unique noise immunity and sensitivity by sampling only small elements of the tread in the footprint, and by being anchored between the tread and tire structure in the area to be sampled. Because the sensor is coupled to a small discrete element of the tread, the system is able to take advantage of the tire gripping action to determine the coefficient of friction when the maneuvering forces within the footprint are very low. In addition, the sensors are able to determine the coefficient of friction at the interface without requiring all elements of the tread within the footprint to slip.

The improved sensitivity is important to the function of the skid warning system. The forces acting on the tread within the footprint are not equal because of variations in the road surface conditions, tread imperfections, and tire deformation-induced forces. As the coefficient of friction reaches a value where the friction can no longer resist the forces exerted by the tire on the roadway, some elements will begin to slip while others will not. This permits the skid warning system to recognize the potential for a skid before the entire footprint begins to slip.

As a typical pneumatic tire rolls along a roadway, the tire deforms within the footprint area to match the contour of the roadway. The deformation of the tire creates forces in the tread, and in the plane of the footprint, referred to herein as gripping forces. As the tire rolls, discrete tread elements (such as 24 of FIG. 1) continually enter and leave the footprint area. A discrete tread element is a portion of tread that touches the roadway as the tire rolls. The element is made discrete by its separation from some part of the tread by a channel or groove, such as a water channeling groove. Most tires on the market today have groove patterns in the tread that provide adequate tread element separation for the methods described herein to work. The tread patterns discussed herein, and shown in FIG. 1 and FIG. 11 are very simple illustrations of discrete tread elements. More complex tread patterns will work just as well.

A discrete tread element, just before entry into the deformed footprint, has no forces acting on its surface; thus a sensor 46 or 50 embedded as described herein would register no force. As the tire rolls, and the discrete tread element enters the footprint, it contacts the roadway and the tire deforms to conform to the roadway. This deformation sets up forces within the tread, and within the plane of the footprint that are resisted by the roadway due to the friction present at the surface of the discrete tread element. The contact force, defined as the force exerted on the discrete tread element by the roadway and acting perpendicular to the footprint plane, changes (according to the characteristics of the tire) as the discrete tread element enters, transits, then leaves the footprint. Similarly, the gripping forces on the same discrete tread element will change (according to the characteristics of the tire) as the discrete tread element enters, transits and leaves the footprint. If, at any time during the discrete tread element's passage through the footprint, the gripping forces, combined with maneuvering forces, exceed the friction forces at the interface, the discrete tread element will slip The slip results in a decrease in the forces acting on the discrete tread element within the plane of the footprint. This change in force is sensed by the tread force sensors. Knowing the forces present on the discrete tread element at the time of the slip, the coefficient of friction in the area where the discrete tread element interfaces with the roadway can be determined using the equation above. The same process applies for forces induced on the discrete tread elements due to maneuvering.

Once the coefficient of friction is known for each tire footprint, that information can be combined with vehicle and tire performance information to generate a skid warning indication. Vehicle stability and control characteristics are determined using existing, well known methods not discussed herein. Similarly, the tire performance characteristics under varying conditions are determined using a combination of testing and analysis according to well established methods.

Operation of the Preferred Embodiment of the Tread Force Sensor

One or more identical sensors 46 (FIGS. 2A and 2B) such as those indicated by 46a and 46b in FIG. 4 are used in each tire. Except for the orientation of reed 40, the installation of each sensor 46 (FIG. 2A) is accomplished in a similar manner. When mounted as described herein, the sensor 46 (FIG. 2A) is rigidly attached to the tire structure by means of tube 30 and disks 32 and 36. Tube 30 passes through the tire structure and holds disk 32 against the inner tire surface 16, and holds disk 36 against the outer tire belt 22 as shown in FIG. 4. As forces are applied to the discrete tread element that contains the reed 40 and gages 44a and 44b, the structure formed by tube 30 and disks 32 and 36 effectively anchors one end of the reed 40 to the tire structure leaving the other end of reed 40 free to deflect as the tread deforms under the influence of the forces present on the tread within the footprint. The strain gages 44a and 44b are attached to the reed 40. Deflection of reed 40 induces strain in gages 44a and 44b which are wired in the arms of a wheatstone bridge such that the output signal is maximized to detect bending in reed 40. Connection of the gages to the bridge circuit is done according to well known methods and not described herein. Tube 30 has a hole running the entire length of the member. The lead wires 38 are routed through the hole 48. This allows the wires to reach the electrical connection to the bridge circuit, amplifiers and slip ring interface within the tire pneumatic cavity. The tube 30 provides a protective environment for the wires, preventing damage due to chaffing and fatigue from forces present in the tire structure. The protective cover 34 protects the gages 44a and 44b from chaffing and fatigue due to forces present in the tread and maintains an air gap 42, shown in FIG. 2B, during the manufacturing process. The air gap 42 is large enough to prevent the tread material from touching the end of the reed 40 as the tread is compressed under the weight of the vehicle or other loads.

In a typical system, at least one sensor 46 (FIGS. 2A and 2B) is placed in the tread as described above such that the reed 40 is oriented at a 45 degree angle to the tire plane of rotation. Thus, when the discrete tread element containing the sensor 46 is in the footprint, the reed will bend as the tread deforms in either the cross-track or in-track directions. The bending of reed 40 induces strain in gages 44a and 44b which generate a signal proportional to the force on the tread.

Longer sensor life and greater sensitivity to coefficient of friction can be gained by using a plurality of sensors 46 equally spaced around the circumference of the tire. In this embodiment, a plurality of identical sensors 46 (FIGS. 2A and 2B) are positioned such that they pass approximately through the center of the footprint with their reeds 40 oriented parallel to the tire plane of rotation. Additional sensors 46 are installed with their reeds 40 oriented about 90 degrees to the tire plane of rotation. The sensors will, as a group, be sensitive to forces acting in any direction within the plane of the footprint. FIG. 4 shows a cross-section of a tire with two sensors 46a and 46b mounted on each side of the tire centerline. With their respective reeds 40 oriented at right angles to each other, one aligned parallel to the tire plane of rotation 46a and the other perpendicular to the tire plane of rotation 46b.

As described above, the forces acting on the tread induce deformation in the tread which results in deformation of the reed 40 and the attached gages 44a and 44b, which then generate a signal proportional to the force present. The lead wires 38 transmit the signal to the bridge circuit and then to the amplifiers shown in FIG. 8.

Description of Alternate Embodiment of Tread Force Sensor

FIG. 3 shows an alternate embodiment of the tread force sensor assembly 50. A structural anchor tube and wire feed-through 52, preferably steel, is threaded on half of its outside surface, opposite the reed attach end, to accept a rigid inner anchor disk 66. A rigid outer anchor disk 70 is permanently attached, such as by welding or other suitable means, to tube 52 near the opposite end leaving room on tube 52 to attach reed 58 and gage 64. Disks 66 and 70 are preferably made of steel. A flexible elongated reed 58, preferably steel, is rigidly attached to the end of tube 52 such that disk 70 is between disk 66 and reed 58, again leaving room for gage 64. A wire feed-through hole 56 is placed in the side of tube 52 and joins with hole 72 that passes through the length of tube 52. A temperature-compensated strain gage 60 is attached to reed 58 by means of a suitable adhesive and lead wires 60a are routed through hole 56 and out of tube 52 through hole 72. A rigid reed anchor 62, preferably steel, is rigidly attached to reed 58 on the end opposite the tube 52 attach point. The angle of attachment between reed 58 and tube 52 is about 90 degrees but can be slightly greater if a greater angle allows support 62 to be closer to the minimum tread line 28 shown in FIG. 5. An additional temperature compensated strain gage 64 is attached to tube 52 approximately centered between the reed 58 attach point and disk 70. Lead wires 64a are routed through hole 56 and out of tube 52 via hole 72.

Figure 5:
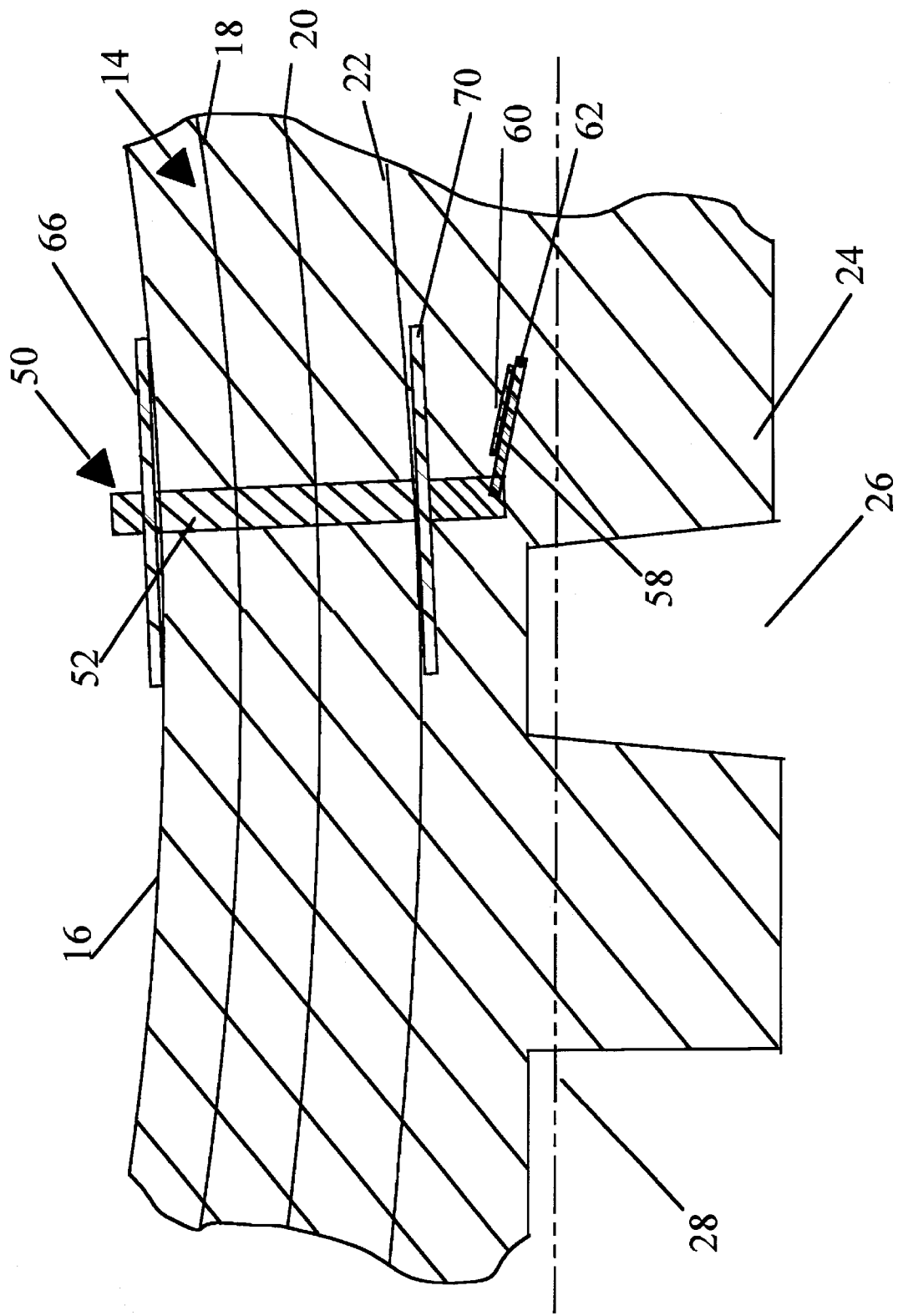
FIG. 5 shows a cross-section of a typical pneumatic automobile tire with the alternate embodiment of the tread force sensor integrated into the tire structure. The figure shows the sensor oriented to sense slippage in the cross-track direction (perpendicular to the tire plane of rotation).

FIG. 5 shows the installation of a tread force sensor assembly 50 in a typical pneumatic automotive tire 14. A cross-track orientation of the sensor 50 is shown where sensor 50 is oriented such that forces within the footprint acting perpendicular to the tire's plane of rotation will place reed 58 in tension or compression.

The number of sensors 50, (FIG. 3) required depends upon the fidelity of coefficient of friction information desired, as well as the type of tire. At least one sensor 50 per tire is required. Unlike the preferred embodiment (shown in FIGS. 2A, 2B and 4), sensor (50 FIG. 3) must be installed in the tire structure before the tread is applied, and preferably before the tire structure is cured.

A typical installation would be accomplished as follows. Referring to FIG. 5, a minimum of one sensor assembly 50 is inserted through the belted layers of the tire structure 14 during the manufacturing process (which is completely known process and not described herein). When the tire structure is complete and all belts 18, 20 and 22 are in place, but before the tread is applied, sensor 50 is inserted through the tire, from the outer tread inward, such that reed 58, and gages 60 and 64 extend beyond the outermost belt 22 and into the region where the tread will be applied. Disk 70 must be firmly seated against the outer belt 22. This is done with disk 66 removed from tube 52 and disk 70 rigidly attached to tube 52 as described above. Once sensor 50 is inserted into the tire structure, disk 66 is threaded on to tube 52 and tightened such that the sensor is rigidly clamping and sandwiching the tire structure between the two disks 66 and 70. Reed anchor 62 is placed in position approximately centered within the discrete tread element 24 in the direction perpendicular to the tire plane of rotation, and near the minimum tread line 28. The length of tube 52, and the distance between the point where reed 58 attaches to tube 52 and disk 70, is such that the entire sensor remains within the tread when the tire is at the end of its useful life, indicated by minimum tread line 28. Next, gages 60 and 64, and lead wires 60a and 64a are coated with a layer of protective material such as is widely used for encapsulating foil strain gages. Such materials and application processes are widely known and not discussed herein.

The orientation of sensor 50 is such that both in-track and cross-track forces are sensed. This can be done by orienting sensor 50 in pairs with their reeds 58 oriented at about 90 degree angles to each other and being either parallel to the tire's plane of rotation or perpendicular to the tire's plane of rotation; or by using a single sensor 50 with its reed 58 oriented at about a 45 degree angle to the tire plane of rotation.

Once all sensors 50 are secured in place, distributed around the tire's circumference as necessary, and reeds 58 have been oriented as described above, the tire tread can be applied using means that are fully known and not discussed herein. After the tire is cured, wire feed-through hole 72, shown in FIG. 3, is potted with epoxy or other suitable material to prevent wire chaffing and to seal hole 72.

FIG. 11 shows a perspective view of a tire section as it will appear after the installation of tread force sensor assemblies 46, 50 or 68.

Operation of Alternate Embodiment of Tread Force Sensor

Theory of Operation

The theory of operation for the alternate embodiment of the tread force sensor 50 in FIG. 3, is the same as that of the preferred embodiment discussed above for sensor 46 in FIG. 2A. Both sensors 46 (FIG. 2A) and 50 (FIG. 3) sense the forces present in the tire tread. Sensor 46 (FIG. 2A) uses a reed 40 in bending, while sensor 50 (FIG. 3) uses a reed 58 in tension or compression to sense tread forces. In addition, sensor 50 incorporates a temperature-compensated strain gage 64 (FIG. 3) mounted to tube 52 to measure the contact force perpendicular to the footprint. Therefore, sensor 50 has the inherent capability to measure contact force.

Operation of the Alternate Embodiment of the Tread Force Sensor

Refer to FIG. 3. When mounted as described herein, sensor 50 is rigidly attached to the tire structure by means of tube 52 and disks 66 and 70. Tube 52 passes through the tire structure and holds disk 66 against the inner tire surface 16 of FIG. 5, and holds disk 70 against the outer tire belt 22 of FIG. 5. As forces are applied to the discrete tread element containing reed 58 and gage 60, the structure formed by tube 52 and disks 66 and 70 effectively anchors one end of reed 58 to the tire structure. Anchor 62 is embedded in the tread material during manufacture of the tire; thus anchor 62 connects the opposite end of reed 58 to the tread. Therefore, as the tread deforms under the influence of the forces present on the tread within the footprint, reed 58 and gage 60 are subject to tread forces that place them in compression or tension. Gage 60 generates a signal just as described in the preferred embodiment, except that gage 60 is connected to the bridge circuit such that the effects of tensile loads on reed 58 are maximized. The connection of gage 60 to the bridge is done according to well established methods not presented herein.

Gage 64 is attached to tube 52 such that the contact force on the discrete tread element can be measured. This is done by ensuring the end of tube 52 is embedded within a discrete tread element 24 such that a line drawn the length of tube 52, and extended outward, will pass continuously through the tread material to the roadway.

FIG. 5 shows a cross-section of a tire with sensor 50 installed. The friction force present at the interface between the discrete tread element and the roadway is very dependent on the contact force, (i.e. the force acting in a direction perpendicular to the plane of the footprint). This can be estimated for a particular vehicle by various methods well known and not discussed herein; however, measurement of the contact force greatly increases the accuracy of the coefficient of friction determination. Gage 64 generates a signal proportional to the force exerted on tube 52 by the discrete tread element 24. Gage 64 is connected to a bridge circuit and wired to maximize sensitivity to tensile loads according to well known means.

In a typical installation, at least one sensor 50 is installed with reed 58 oriented at about a 45 degree angle to the tire plane of rotation such that forces within the plane of the footprint can be sensed as tension or compression on the reed 58 and gage 60. Improved sensitivity and life can be achieved by using a plurality of sensors about equally spaced around the circumference of the tire and equally spaced on each side of the tire centerline. About half of sensors 50 on each side of the tire centerline are oriented with their reeds 58 at about 90 degree angles to the tire plane of rotation. The remaining sensors are oriented with their reeds 58 about parallel to the tire plane of rotation.

Description of Contact Force Sensor

Figure 7:
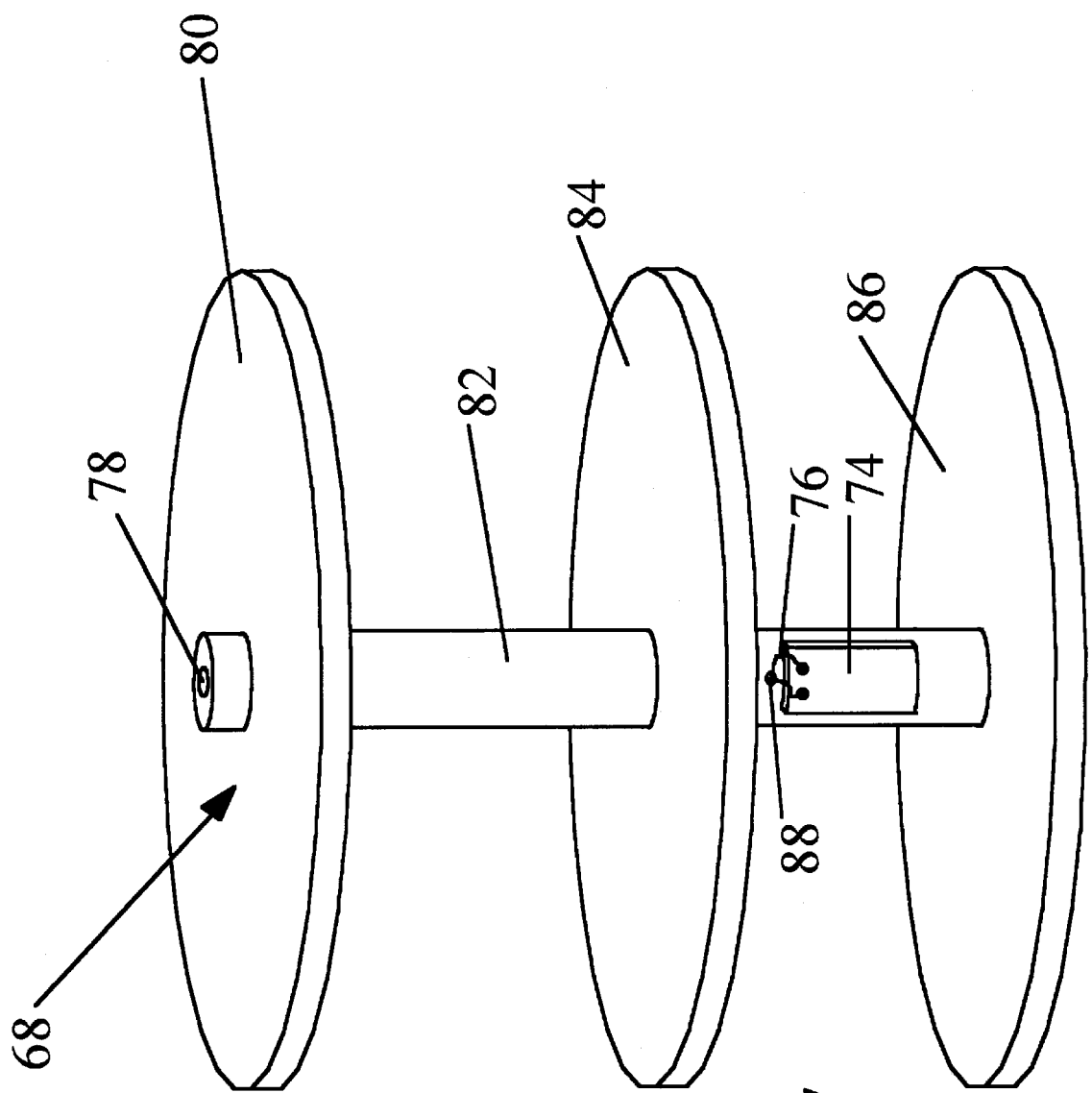
FIG. 7 shows a perspective view of the contact force sensor.

FIG. 7 shows a perspective view of the contact force sensor assembly 68. A rigid, structural anchor tube and wire feed-through 82, preferably steel, is threaded along a quarter of its length, on its outside surface to accept a rigid, inner anchor disk 80. A rigid, outer anchor disk 84 is permanently attached, such as by welding or other suitable means, to tube 82, near the middle of tube 82, leaving room to attach a temperature-compensated strain gage 74 to the side of tube 82, and a rigid, preferably steel force distribution disk 86. Disk 86 is rigidly attached, such as by welding or other suitable means, to the end of tube 82 opposite disk 80 such that gage 74 is between disk 84 and disk 86. A wire feed-through hole 88 is placed in the side of tube 82 and joins with a wire feed-through hole 78 that passes through the length of tube 82. A temperature-compensated strain gage 74 is attached to tube 82 by means of a suitable adhesive, and strain gage lead wires 76 are routed through hole 88 and out of tube 82 through hole 78.

Figure 6:
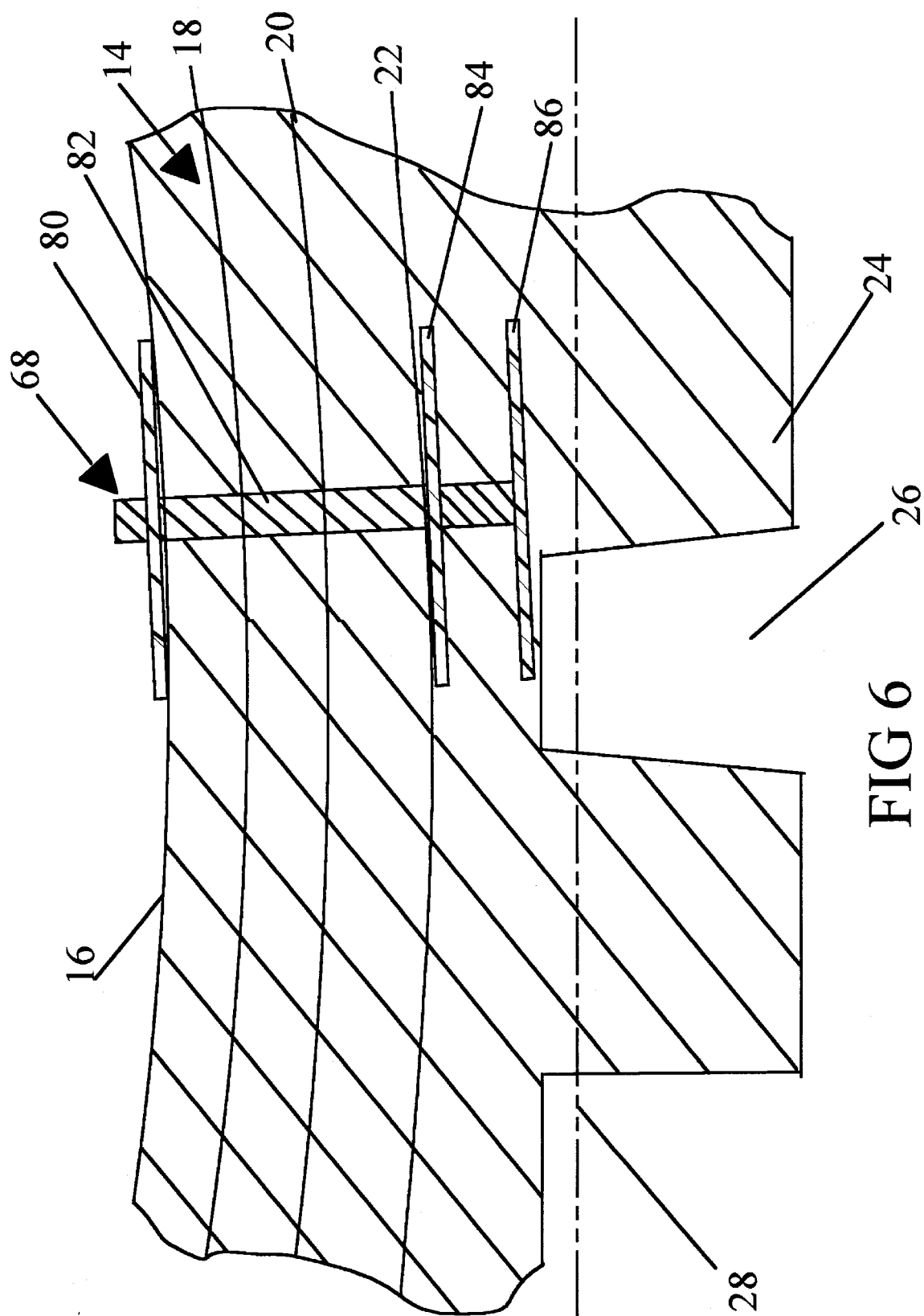
FIG. 6 shows a cross-section of a typical pneumatic automobile tire with the contact force sensor integrated into the tire.

FIG. 6 shows a cross-section of sensor assembly 68 installed in a typical pneumatic automotive tire. Installation of sensor 68 is accomplished by unscrewing disk 80, and inserting tube 82 of sensor assembly 68 through the tire structure before the tire tread is applied, and preferably before the tire structure is cured. Tube 82 is inserted through the structure from the outside of the tire such that disk 84 is firmly seated against the outer belt 22 of the tire. Then disk 80 is threaded onto tube 82 such that the tire structure is tightly clamped and sandwiched between disks 80 and 84. The length of tube 82 from disk 84 to disk 86 occupies the region where the tire tread is to be applied. The sensor must be positioned such that disk 86 is at least half way covered by a discrete tread element contacting the roadway 24. Thus, a line drawn through the center of tube 82 and extended outward to the roadway will pass continuously through tread material. The remaining portion of disk 86 can be covered by just a thin layer of tread and a channel 26 if necessary to fit the tire tread pattern.

Operation of Contact Force Sensor
Operation of the Contact Force Sensor

Sensor 68 in FIG. 6 is designed to measure the contact forces present on a discrete tread element 24 in contact with the roadway. The operation is essentially the same as that of the contact force sensor incorporated in sensor 50, gage 64 shown in FIG. 5. Sensor 68 is intended to supplement sensors 46 and 50 when improved contact force measurements are desired to improve the accuracy of the coefficient of friction determination system discussed above.

FIG. 7 shows the construction of sensor 68. Tube 82 passes through the tire structure and holds disks 80 and 84 firmly against the tire structure as described for sensors 46 and 50. A temperature-compensated strain gage 74 is attached to tube 82 and generates a signal in proportion to the force on tube 82. Disk 86 is attached to tube 82 and acts to focus the force distributed on the discrete tread element 24 in FIG. 6, onto the end of tube 82. FIG. 6 shows a cross section of sensor 68 installed in a typical pneumatic tire. As the tire rotates such that sensor 68 is in the footprint, the force perpendicular to the plane of the footprint passes through the tread element containing sensor 68; thus the force also passes through sensor 68 and causes gage 74 to deliver an electrical signal in proportion to the force in tube 82.

Figure 8:
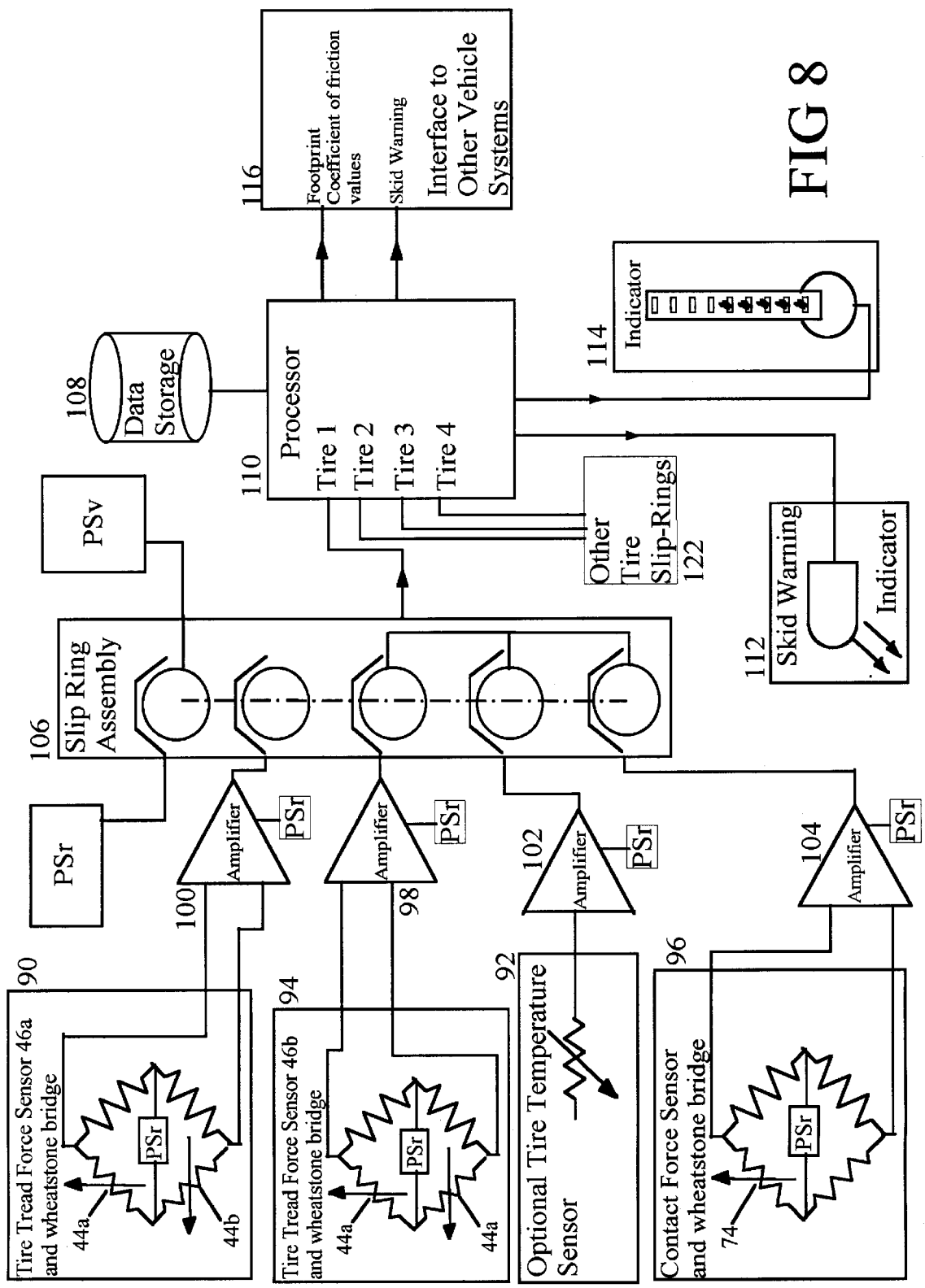
FIG. 8 shows a functional diagram for the preferred embodiment of the coefficient of friction monitor, coefficient of friction qualitative indicator and skid warning indicator system.

Description of Preferred Embodiment of Coefficient of Friction Monitor and Skid Warning System FIG. 8 is a functional flow diagram illustrating the parts of the preferred embodiment of a coefficient of friction monitor and skid warning indicator system. FIG. 8 shows the system for a single tire. All components in FIG. 8 except for processor 110, skid warning indicator 112, interface 116, and data storage 108 are duplicated for each vehicle tire. Additional sensors can be added to each tire to increase the fidelity of the coefficient of friction information; and thereby increase the effectiveness of the skid warning system.

Each of a vehicle's four typical pneumatic automotive tires is fitted with two tread force sensors 46a and 46b (as shown in FIG. 4), and one contact force sensor 68 (shown in FIG. 6). Contained within each tire pneumatic cavity (or attached to the wheel hub) are three wheatstone bridge circuits 90, 94 and 96. Each sensor 46 and 68 is connected to its own bridge circuit. Also contained within each tire, is a signal conditioner and amplifier 98, 100 and 104 for each bridge circuit. The output of each signal conditioner and amplifier 98, 100, 102 and 104 is routed through the pneumatic cavity in the tire to the rotating portion of a slip ring assembly 106 located on the axle or hub of each wheel. Each signal conditioner and amplifier has its own channel on the slip ring. Signal conditioning and amplifiers 98, 100, 102, 104 enhance the signal output from each sensor and simplify the interface with the processor circuitry according to well known means that are not discussed herein. Power for the bridge circuits and signal conditioners, and amplifiers, comes from a distribution point within the tire, PSr, which receives power via slip ring assembly 106, and the vehicle electrical power system PSv.

In applications where temperature-compensated strain gages cannot be used in sensors 46 and 68, or can not compensate over the entire tire operating temperature range, a tire temperature sensor 92 can be added to each tire's tread region. Temperature sensor 92 (FIG. 8) connects to a signal conditioner and amplifier 102 appropriate for the type of temperature sensor selected, and connects to the rotating portion of the slip ring assembly 106. Selection of temperature sensors, and the appropriate signal conditioning and amplification means are well known and not discussed herein. Likewise, the method of compensating strain gages for variations in operating temperature are well known and not discussed herein.

The non-rotating portion of slip ring assembly 106 connects to a processor 110. Processor 110 receives conditioned tread force sensor information via slip ring assembly 106 for each vehicle tire and for each sensor. Processor 110 can access stored data located in a data storage device 108. Such data storage can be an integral part of processor 110. The design of processor 110 and data storage 108 are well known and not described herein. Data storage 108 contains at least:
(a) a predetermined numerical model of the motor vehicle handling characteristics,
(b) at least one predetermined reference coefficient of friction value
(c) at least one predetermined tire performance characterization value,
(d) storage for variables used by processor 110, The predetermined numerical model of the motor vehicle handling characteristics describes the vehicle handling characteristics and defines a safe operating envelope. Inputs to the model are the predetermined values above, and three input variables:
(a) vehicle speed,
(b) at least one footprint coefficient of friction imbalance variable, and
(c) at least one tire performance characterization variable.

The model is operated on by processor 110 to determine the proper conditions to generate the skid warning. Vehicle speed is determined by the processor using the tread force sensor information. The footprint coefficient of friction imbalance variable is determined by the processor 110 as described below. The tire performance characterization variable is an indication of the tire's tread force and tread slip behavior. The tire performance characterization variable is set equal to the predetermined tire performance characterization value stored in data storage 108.

Processor 110 connects to a skid warning indicator 112 mounted within the view of the vehicle operator. Processor 110 also connects to an LED bar-graph indicator assembly 114, or other suitable display device, mounted within the view of the vehicle operator. Processor 110 makes all processed and preprocessed tire sensor, and footprint coefficient of friction information available to other vehicle systems (such as anti-skid brake systems) in the form of electronic signals via an interface to other vehicle systems 116. The nature of the signals depends upon the requirements of other vehicle systems 116 interface. Interfaces to other vehicle systems 116 are done by well established methods not discussed herein.

Processor 110 is connected to the three other tires via 122. The system for the other tires is identical the system shown in FIG. 8 wherein only items 90, 94, 92, 96, 100, 98, 102, 104, and 106 are duplicated for each tire.

Operation of Preferred Embodiment of Coefficient of Friction Monitor and Skid Warning System Refer to FIG. 8. Sensors 46 and 68 sense-the force in the tire tread as described above. Each sensor is connected to a wheatstone bridge circuit 90, 94 and 96. The signals are conditioned and amplified by a signal conditioner and amplifier 98, 100 and 104 as described above, and transferred across the rotating tire/vehicle interface by a slip ring assembly 106. Slip ring assembly 106 connects the signals from each tire sensor to a processor 110.

Processor Operation, and Use of Predetermined Values, Numerical Model and Variables Processor 110 uses at least one predetermined reference coefficient of friction value, a predetermined numerical model of the motor vehicle handling characteristics, at least one predetermined tire performance characterization value, combined with the tread slip behavior and tread force information, to determine the footprint coefficient of friction value for each tire and to generate the skid warning according to the theory above.

The at least one predetermined reference coefficient of friction value serves as an initial value to initiate skid warning indication 112. When the footprint coefficient of friction under one or more tires approaches the reference coefficient of friction value, skid warning indication 112 is activated.

As processor 110 receives more samples of tread forces and tread slip behavior, processor 110 modifies the reference coefficient of friction value according to the numerical model described below.

The footprint coefficient of friction is determined based on the tread slip behavior and tread forces measured by the tread force sensors described above. Processor 110 further uses the at least one predetermined tire performance characterization value to adjust the initially determined footprint coefficient of friction values to improve their accuracy. The predetermined tire performance characterization value is an empirically derived parameter that relates a tire's tread force and tread slip behavior to the footprint coefficient of friction.

The numerical model describes the vehicle handling characteristics and defines a safe operating envelope. The three input variables: vehicle speed, at least one footprint coefficient of friction imbalance variable, and at least one tire performance characterization variable are determined by processor 110 as described below, and input to the model. The output of the numerical model is a skid warning initiation, and an adjusted reference coefficient of friction value. The reference coefficient of friction can be adjusted to fine tune the point where a skid warning should be initiated. For example, the reference value would be increased if processor 110 determines that excessive tread slip is occurring before the footprint coefficient of friction values approach the predetermined value for the reference. Thus, the system is capable of dynamically adjusting appropriate parameters to optimize its function.

The three variables used in the numerical model are determined by processor 110 as follows:
(a) vehicle speed is determined by monitoring the transitions on the at least one force sensor on each tire, where the force sensor output transitions are indicative of tire RPM's, and speed is derived from the RPM's according to well established methods.
(b) The footprint coefficient of friction imbalance variable is determined by processor 110 based on the difference between the determined footprint coefficient of friction under each tire. The imbalance parameter is important because it represents a potential for uneven force to be applied to each tire, such as during braking.
(c) The tire performance characterization variable is retrieved from data storage 108 wherein a predetermined tire performance characterization value is stored as described above.

These three variables are determined by processor 110 and input to the numerical model along with the tread slip behavior and footprint coefficient of friction under each tire. Processor 110 operates on the numerical model and yields a skid warning indication when the numerical model indicates the vehicle is approaching an unsafe operating condition.

The skid warning indication takes the form of a dashboard-mounted skid warning indication 112 that illuminates at processor 110 command to warn the vehicle operator of a potential skid. Illumination of skid warning indicator 112 tells the vehicle operator that the coefficient of friction under the tires is too low to safely operate the vehicle under existing conditions. Upon illumination of the skid warning indicator 112, the vehicle operator should slow down carefully, or stop the vehicle entirely depending on the roadway conditions.

In addition to a skid warning indicator 112, an LED bar-graph indicator 114, or other suitable display device, is driven by processor 110 to display a qualitative indication of the footprint coefficient of friction between the tires and roadway. In the preferred embodiment, indicator 114 reads full-scale when the footprint coefficient of friction is characteristic of a normal, clean, dry roadway and normal tire performance. Indicator 114 reads very low at a point where the footprint coefficient of friction is very low, such as would be experienced just before skid warning indicator 112 illuminates.

In addition to generating the two indicators just discussed, processor 110 will generate a footprint coefficient of friction signal for each tire, and make it available via an interface 116, to other vehicle systems such as antiskid brake systems, automatic traction control systems or any other system that could benefit from roadway coefficient of friction information.

Figure 9:
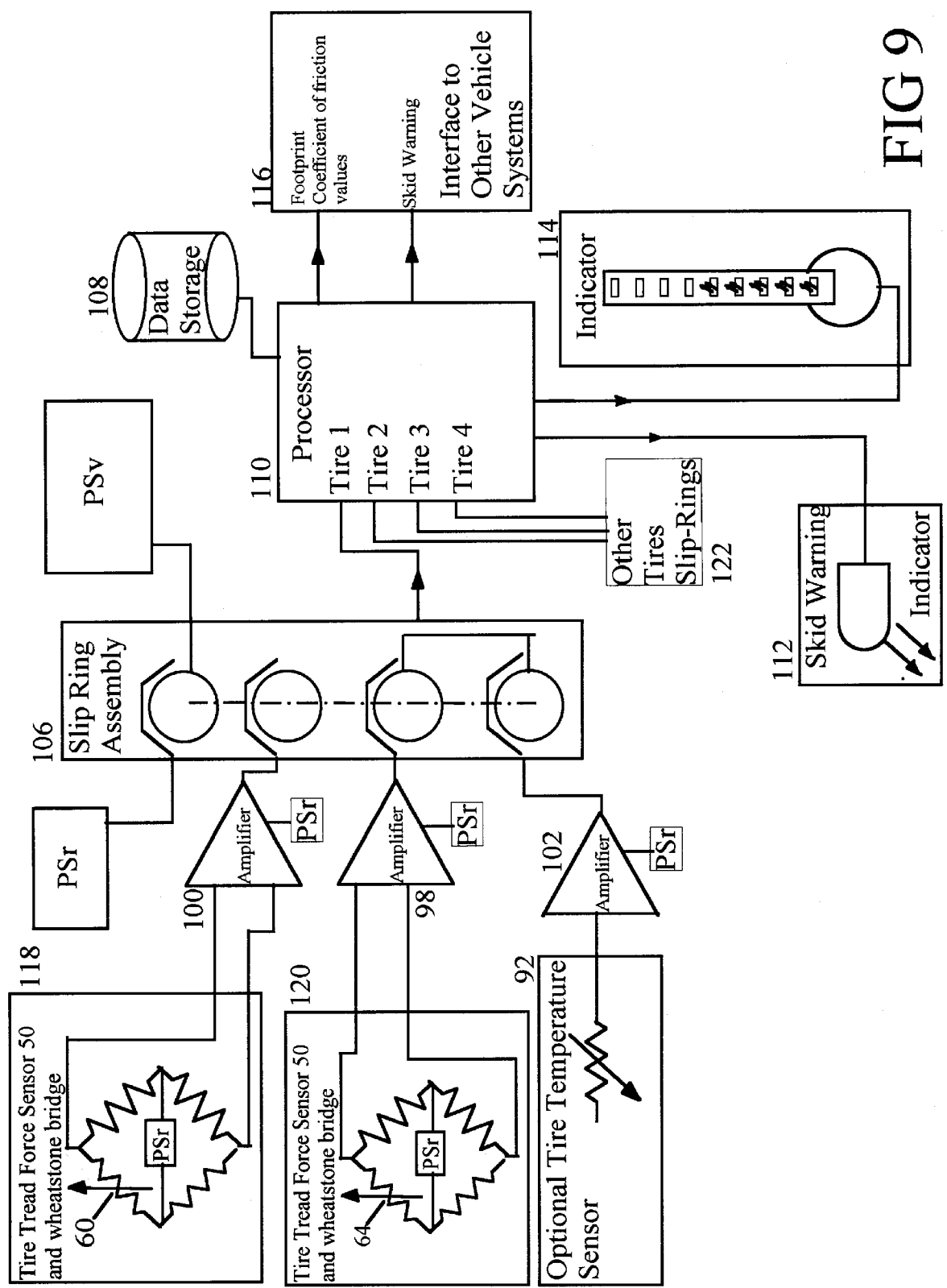
FIG. 9 shows a functional diagram for the alternate embodiment of the coefficient of friction monitor, coefficient of friction qualitative indicator and skid warning indicator system.

Description of Alternate Embodiment of Coefficient of Friction Monitor and Skid Warning System Refer to FIG. 9. The alternate embodiment is the same as the preferred embodiment described above; except that the sensors 46 (FIG. 2A) and 68 (FIG. 7) are not used. In their place, sensor 50 (FIG. 3) is used to sense contact pressure and tread forces in the plane of the footprint. Sensor 50 is installed in the tire as described above. A typical installation would use sensor 50 installed in each of the vehicle's tires as described for the alternate embodiment above. Gage 60 of each sensor 50 connects to a wheatstone bridge 118 and then to a signal conditioner and amplifier 100, and to processor 110 via the slip ring assembly 106 as described for the preferred embodiment. Likewise, gage 64 of each sensor 50 connects to a wheatstone bridge 120 and then to a signal conditioner and amplifier 98, and to processor 110 via the slip ring assembly 106 as described for the preferred embodiment.

Operation of Alternate Embodiment of Coefficient of Friction Monitor and Skid Warning System The function of the alternate embodiment is the same as the function of the preferred embodiment described above. The only difference is sensor 50 (FIG. 3) replaces sensors 46 (FIG. 2A) and 68 (FIG. 7). Sensor 50 supplies the same information to processor 110 as sensors 46 (FIG. 2A) and 68 (FIG. 7).

Figure 10:
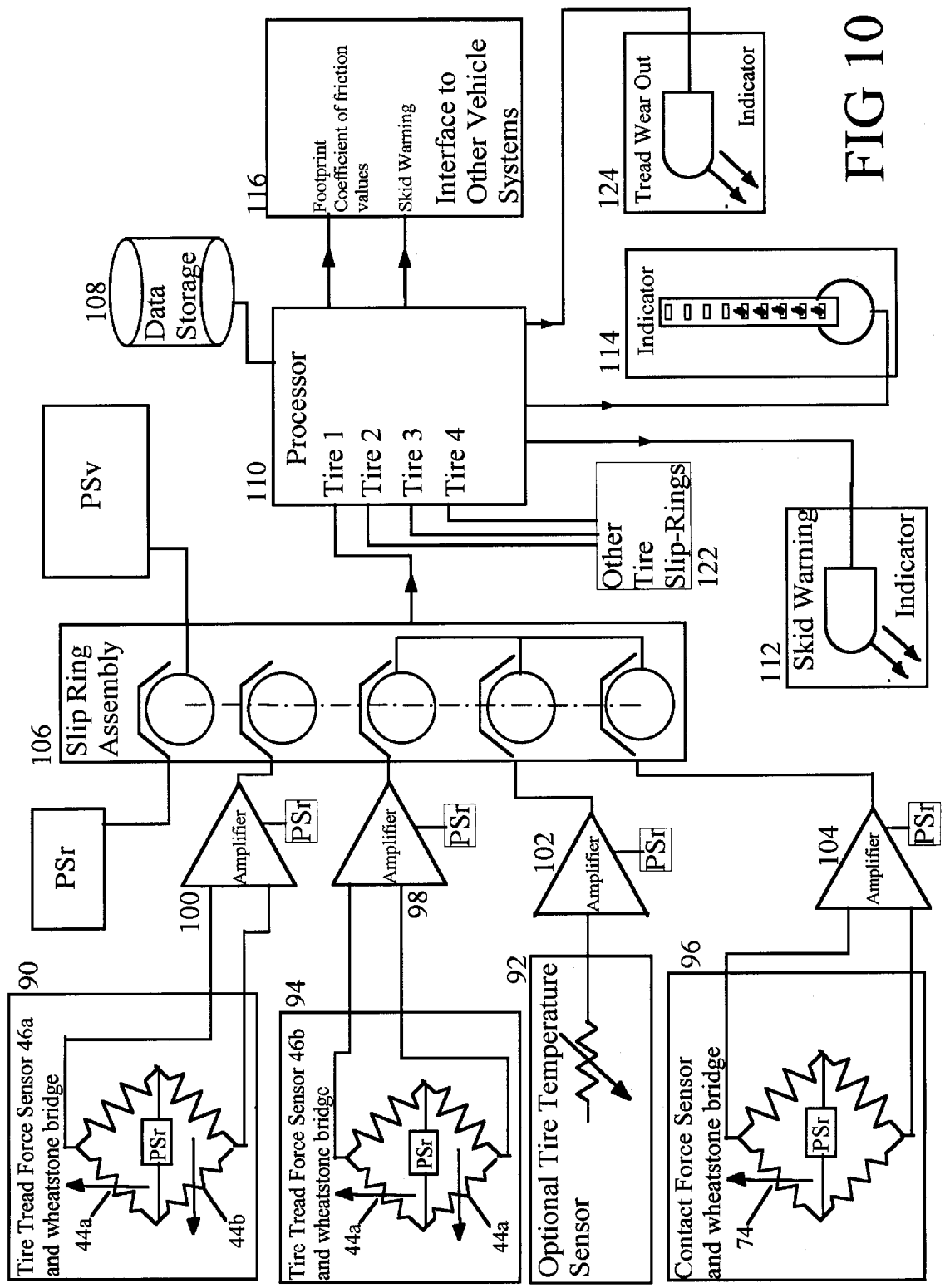
FIG. 10 shows a functional diagram for the preferred embodiment of the coefficient of friction monitor, coefficient of friction qualitative indicator and skid warning indicator system, with the added tire tread wear out indication.

Description of Preferred Embodiment of Coefficient of Friction Monitor and Skid Warning System with Added Tread Wear Indication Refer to FIG. 10. In addition to the skid warning and coefficient of friction indications described above for the preferred embodiment of the coefficient of friction monitor and skid warning system (FIG. 8), the expanded system shown in FIG. 10 provides a tire tread wear out indication 124, and at least one additional predetermined tread wear value per tire is added to data storage 108. Tire tread wear out indicator 124 is added to the system and connected to processor 110.

Operation of Preferred Embodiment of Coefficient of Friction Monitor and Skid Warning System with Added Tread Wear Indication The theory and method of operation of the tread force sensors and other components are the same as previously discussed for FIG. 8 with the following modifications.

As shown in FIG. 10, processor 110 monitors the tread slip behavior and tread forces, and determines the amount of tread wear. As the tread wears away, the forces and tread slip behavior will change. This is especially true for the tire gripping forces described above. Processor 110 monitors these parameters and adjusts the tire performance characterization value for each tire to reflect the tire performance given the tread wear condition of each tire. Therefore, as the tire tread wears, processor 110 adjusts the tire performance characterization value, which is then used to determine the proper conditions to trigger skid warning indication 112. Also, processor 110 compares the tread wear condition of each tire with the predetermined tread wear value and initiates the tire tread wear out indication 124 as the determined tread wear approaches the predetermined tread wear value contained in data storage 108.

Conclusion, Ramifications and Scope of Invention

Thus the reader will see that the invention described herein provides:

(a) a method and system to determine the coefficient of friction within the footprint of a single tire in contact with a rolling surface, at least once each revolution, by monitoring only a discrete element of the tread within the footprint such that the forces present on that discrete element of tread are sensed as the portion passes through the footprint. Slipping of the discrete tread element is determined by a change in the forces on the tread portion that are not associated solely with the portion entering or leaving the footprint.

(b) a method to detect the slippage of a discrete element of the tread within the footprint of a rolling tire, that does not require slippage of all tread within the footprint. In other words, slippage of the entire footprint area, and a resultant change in wheel rotational speed is not required to determine the coefficient of friction in the footprint.

(c) a method of monitoring the forces on a discrete element of tread within the footprint of a rolling tire sensitive enough to detect the slippage of that discrete element of tread under very light maneuvering loads, or by sensing the gripping forces of the pneumatic tire under approximately zero maneuvering loads.

(d) a method of detecting the forces on a discrete element of tread within the footprint of a rolling tire while isolating the sensor from stresses and forces in the tire structure; thus minimizing the ability of various noise sources to couple into the sensor, reducing the processing required to extract meaningful coefficient of friction information, and eliminating the need for information from other sensors (such as accelerometers, tire temperature sensors, and tire pressure sensors).

(e) a method of detecting the forces on a discrete element of tread within the footprint of a rolling tire by means of a sensor assembly that can be incorporated into a conventional tire without extensive redesign of the tire structure, or the tread materials.

(f) a method of detecting the forces on a discrete element of tread within the footprint of a rolling tire by means of a sensor assembly that can be installed in a tire after the tire manufacture is completed.

(g) a system whereby the coefficient of friction is determined from the forces sensed in a discrete element of tread within the footprint of a rolling tire, such that the coefficient of friction is presented to the operator of the vehicle in the form of a qualitative assessment of roadway coefficient of friction as well as a skid warning indication.

(h) a method to generate a tread wearout indication and to monitor tread wear using tread slip behavior and tread force information.

To summarize, the invention provides a method to determine accurately the coefficient of friction under each of a vehicle's tires, and provides a method to convert the tread force sensor data into information useful to the vehicle operator and other vehicle systems. The availability of such data will greatly increase the safety and efficiency of all vehicles that rely upon contact friction within the tire/roadway interface for proper operation.

While my above description contains many specificities, these should not be construed as limitations on the scope of the invention, but rather as an exemplification of two embodiments thereof. Many other variations are possible. For example:

(a) the number of tread force sensors can be increased or decreased. In both embodiments described herein a minimum of one tread force sensor is required for each tire. A greater number of sensors distributed across the footprint and around the circumference will yield higher fidelity tread force data, and improve the reliability of the coefficient of friction monitor and skid warning system. For example, if a nail or other failure mechanism causes a sensor to fail, the processor can filter data from the defective sensor to prevent serious degradation of the overall skid warning and coefficient of friction monitoring system.

(b) The contact force sensor can be eliminated from both the preferred and alternate embodiments. The contact force under each tire can be estimated by various well known methods. In many cases, the estimate will be accurate enough to provide accurate coefficient of friction information.

(c) The sensors described herein use foil-type strain gages; however, any strain sensing element can be used to achieve the same result. The wheatstone bridge, and signal conditioner and amplifiers are modified (or eliminated) as required to properly interface the selected sensor to the processor according to established methods.

(d) The materials used to construct the tread force sensors and contact force sensor can be any rigid material capable of sustaining the operating loads in the tread.

(e) The reed used in sensors 46 and 50 can be eliminated if not required by the strain gage, or displacement sensor selected. The reed is provided to limit the elongation of the strain gage; thus prolonging cycle life. For strain gages, or displacement sensors that do not require this support, the reed can be eliminated. In its place, the strain, or displacement sensing member is anchored directly to the structural anchor and wire feed-through tubes at one end, and to the tread (by use of a suitable anchoring means such as a pin, or T-shaped member) at the other end.

(f) The inner and outer anchoring disks used in sensors 46, 50, and 68 can be eliminated or of a different shape than described herein. The structural anchor and wire feed-through tubes can be glued in place with a suitable adhesive or held in place by interference fit with the surrounding tire structure. Similarly, a single anchor disk can be used such that the disk is sandwiched between the layers of the tire structure (for example between the inner 18 and outer belts 22, FIG. 1).

(g) Displacement sensors can be used in place of the strain gages. The forces exerted on the tread will cause elastic deformation of the tread. A displacement sensor can sense the deformation in the tread. Thus, the deformation, combined with empirical data on the tire and its materials, allows the determination of the corresponding force. The wheatstone bridge, and signal conditioner and amplifiers are modified (or eliminated) as required to properly interface the selected sensor to the processor according to established methods.

(h) The skid warning indicator is not required. A useful system may only provide coefficient of friction information to automated systems. No display for the vehicle operator is required. The skid warning can be delivered electronically to automatic systems on the vehicle such that these systems can take appropriate action without intervention by the vehicle operator.

(i) The skid warning indicator can be replaced by an audible signal, or any other signal whose output can be directly perceived by the vehicle operator.

(j) The LED bar-graph indicator and the related function can be eliminated.

(k) The number of LED bar-graph indicators, or other suitable displays capable of fulfilling the same function can be increased from one per vehicle to one per tire.

(l) The LED bar-graph indicator can be replaced by any other display suitable for providing qualitative information to the vehicle operator. In addition, the indicator can be replaced by an audible signal, or any other signal whose output can be directly perceived by the vehicle operator.

(m) The slip ring assembly can be replaced by any means capable of passing the sensor signals across the rotating interface between the tire and the vehicle.

(n) A long-life battery contained within the tire, (or attached to the rotating portion of the wheel) can replace the vehicle power system in powering the sensors and associated electronics within the rotating tire. This will allow the use of slip rings or other interfaces which are incapable of transmitting power across the rotating interface (such as optical interfaces).

(o) The processor can be eliminated and replaced by a suitable circuit, such as a comparitor circuit, which generates an analog signal proportional to the sensor output. This analog signal can be used to drive the various vehicle operator displays, and provide coefficient of friction information to vehicle systems.

(p) The processor can be eliminated and replaced by a suitable circuit such as a comparator circuit, which can signal a skid warning when the sensor output drops below a particular threshold.

(q) Data storage device and related data can be eliminated if the processor is replaced by a comparator or other suitable circuitry.

(r) The tire temperature sensor can be eliminated. Temperature-compensated strain gages and displacement sensors will not need tire temperature information to compensate for sensor signal changes caused by temperature variations.

(s) The tire temperature sensor can be replaced by a thermistor, or other temperature sensitive component, in the wheatstone bridge circuit, or in the signal conditioning and amplifier circuit. Since these components are located within the tire, these circuits can be designed to sense and compensate for tire temperature effects according to well established methods.

(t) While optimized for vehicle tires, the system described herein has other uses. For example, sensors described herein can be incorporated into rollers or tires used to feed paper in a paper mill, copier or printer. Rollers and tires so equipped will sense forces in the footprint area, between the sensor-equipped member and it rolling surface. Thus, the signal generated by the sensors can be used to:
  (i) adjust the feed mechanism to ensure proper handling of different papers,
  (ii) compensate for humidity effects on the paper thickness and surface texture,
  (iii) compensate for varying paper thickness
  (iv) detect paper jams (u) Sensors described herein can be incorporated into rollers or tires used in various material feed mechanisms to detect slipping belts, or other material passing over sensor-equipped rollers and tires.

(v) The sensors, tread force sensing methods and coefficient of friction determination methods outlined herein can be used effectively in nonpneumatic tires such as solid rubber, or foam-filled tires. The invention is not limited to pneumatic tires.

(w) The skid warning system can be used to detect hydroplaning of one or more vehicle wheels since hydroplaning results in a very low effective coefficient-of friction within the footprint.

(x) The system described herein is designed to sense forces between a discrete tread element and the tire structure; however, a sensor anchored between two tread elements and isolated from the tire structure can provide similar tread force and slip information, particularly if the two elements are on opposite sides of the tire centerline.

(y) Disk 86 of sensor 68 shown in FIG. 7 can be omitted.

(z) Gage 74 on sensor 68 can be moved from its attachment point on the side of tube 82 to either side of disk 58.

Accordingly, the scope of the invention should be determined not by the embodiments illustrated, but by the appended claims and their legal equivalents.

We claim:

1. A method for generating a skid warning for a motor vehicle on a road surface comprising,
  a) monitoring the tread slip behavior of at least one discrete tread element within the footprint of at least one tire;
  b) using said tread slip behavior of said discrete tread element to determine a footprint coefficient of friction value between said tire and said road surface, by measuring the forces on said discrete tread element;
  c) comparing said footprint coefficient of friction value with at least one predetermined reference coefficient of friction value;
  d) generating said skid warning when said footprint coefficient of friction value approaches said predetermined reference coefficient of friction value;
  e) whereby said footprint coefficient of friction value can be determined using said tread slip behavior from the single tire in contact with said road surface, and said skid warning is achieved by sensing the slip of said discrete tread element before all the discrete tread elements within said footprint slip.

2. A method according to claim 1, further including incorporating an indication means to convey said skid warning to a vehicle operator, whereby the operator is made to perceive said skid warning.

3. A method according to claim 1, further including using an indication means to provide said footprint coefficient of friction value to a vehicle operator, whereby the operator is made to perceive said footprint coefficient of friction value.

4. A method according to claim 1, further including incorporating an interface means to provide said skid warning to other motor vehicle systems, whereby the motor vehicle systems are enabled to receive said skid warning.

5. A method according to claim 1, further including incorporating an interface means to provide said footprint coefficient of friction value to other motor vehicle systems, whereby the other motor vehicle systems are enabled to receive said skid warning.

6. A method according to claim 1, further including using a processing means to determine said footprint coefficient of friction value from said tread slip behavior and the forces on said discrete tread element, and compare said footprint coefficient of friction value with said predetermined reference coefficient of friction value, and generate said skid warning when said footprint coefficient of friction value approaches said predetermined reference coefficient of friction value.

7. A method according to claim 6, further including using said processing means to compare said footprint coefficient of friction value for at least two tires and generating at least one footprint coefficient of friction imbalance value in proportion to the difference between the footprint coefficient of friction values.

8. A method according to claim 7, further including incorporating a predetermined numerical model of the motor vehicle handling characteristics, wherein the model includes at least one vehicle speed variable, at least one footprint coefficient of friction imbalance variable, and at least one predetermined tire performance characterization variable; whereby the processing means generates said skid warning dependent on the value of the variables and said footprint coefficient of friction for each monitored tire.

9. A method according to claim 1 further including incorporating a tire tread wear out indication means and at least one predetermined tread wear coefficient value and a processing means; whereby said tread slip behavior and the tread forces are compared to said predetermined tread wear value and said tire tread wear out indication means is activated when said tread slip behavior and the tread forces approach said predetermined tread wear coefficient value; and whereby tires with abnormal tread wear are sensed and said tire tread wear out indication is perceived by the vehicle operator.

10. A method for determining the coefficient of friction between a single motor vehicle tire and the road surface comprising, a) monitoring the tread slip behavior of at least one discrete tread element within the footprint of the tire;

b) using said tread slip behavior from said discrete tread element to determine a footprint coefficient of friction value by measuring the forces on said discrete tread element;

c) whereby said footprint coefficient of friction value can be determined by the forces and tread slip behavior of said discrete tread element.

11. A method according to claim 10, further including incorporating at least one tread force sensing means within said tire, wherein said tread force sensing means is anchored between the tire structure and said discrete tread element; whereby the forces acting on said discrete tread element, and resisted by the tire structure, are sensed.

12. A method according to claim 11, further including using a plurality of said tread force sensing means spaced about uniformly around the tire circumference, and about uniformly across the tire footprint, and each said tread force sensing means monitoring one said discrete tread element; whereby said discrete tread elements sample the tire footprint each tire revolution.

13. A method according to claim 10, further including using a processing means, at least one predetermined tire performance characterization value, in combination with the tread forces, to determine said footprint coefficient of friction value; whereby the accuracy of said footprint coefficient of friction value is improved.

14. A method according to claim 11, further including using at least one said tread force sensing means wherein said tread force sensing means is oriented to measure the tread forces within the footprint acting in a direction about perpendicular to the tire plane-of-rotation; whereby tire gripping forces, tire deformation induced forces and said tread slip behavior can be monitored, and said footprint coefficient of friction value can be determined when maneuvering loads are about zero.

15. An apparatus for determining forces acting on a discrete tire tread element within the footprint of a motor vehicle tire comprising, a) a sensing means that is at least partially embedded within said discrete tire tread element for sensing said forces acting on said discrete tire tread element;

b) an anchoring means for said sensing means, wherein one end of said sensing means is anchored to the tire structure and the other end of said sensing means is anchored to said discrete tire tread element;

c) a feed through means to enable the electrical connections of said sensing means to pass without damage from the region of the tire containing said sensing means, through the tire structure, to the tire hub;

d) whereby said sensing means is anchored to said discrete tread element on one end and to the tire structure on the other end, and said forces acting on said discrete tire tread element and resisted by said tire structure are sensed, and said electrical connections are protected as they pass between said sensing means and said tire hub, and further whereby the forces on an individual discrete tread element are determined.

16. An apparatus according to claim 15, wherein said sensing means is a strain sensing device mounted by suitable attaching means, on an elongated reed of predetermined size and material properties; whereby force exerted on said elongated reed is sensed by said strain sensing device, and said elongated reed provides mechanical support to said strain sensing device, and thereby prevents damage to said strain sensing device.

17. An apparatus according to claim 16 wherein said elongated reed is oriented with the longest axis of said elongated reed about perpendicular to the plane of the tire footprint, and the end of said elongated reed closest to the tire tread is fixed in the tire tread, and the end of said elongated reed closest to the tire axis of rotation is anchored to the tire structure; whereby deformation of the tire tread due to incident forces induces bending in said elongated reed, resulting in a signal from the sensing means in proportion to the incident forces.

18. An apparatus according to claim 16, wherein said elongated reed is oriented with the longest axis of said elongated reed about parallel to the plane of the tire footprint, and oriented about between zero and ninety degrees from the tire plane of rotation.

19. An apparatus according to claim 15, wherein said anchoring means includes;

a) a structural anchor tube of predetermined size and material properties passing through said tire structure in the region of the tread, and not passing completely through the tread layer, and oriented with the tube's long axis about perpendicular to the plane formed by the tire footprint;

b) one end of said structural anchor tube protruding into the pneumatic cavity of the tire, and the other end protruding into the tread region but not passing completely through the tire tread;

c) two rigid disks of predetermined size and material properties with a hole in each of said rigid disks and said hole sized to admit said structural anchor tube;

d) one of said rigid disks positioned against the inner surface of the pneumatic tire within the pneumatic cavity such that said structural anchor tube passes through said hole in the disk;

e) the second of said rigid disks positioned against the outer surface of the tire structure between the tire structure and the tire tread such that said structural anchor tube passes through said hole in the disk;

f) both of said rigid disks secured to said structural anchor tube by an attaching means, whereby the tire structure is tightly sandwiched between said rigid disks, and said structural anchor tube is held firmly to the tire structure.

20. An apparatus according to claim 19, wherein said rigid disk positioned against the outer surface of the tire structure between the tire structure and the tire tread is omitted, and said disk positioned against the inner surface of the tire structure and said structural anchor tube are held in place by an adhesive means, or the said disk positioned against the inner surface of the tire structure and said structural anchor tube are held in place by friction forces acting between said structural anchor tube and said tire structure where said structural anchor tube passes through a preformed hole in said tire structure; whereby the apparatus can be installed into said preformed hole after the tire tread is applied to the tire structure, and said structural anchor tube is firmly held in the preformed hole.

* * * * *